(12) United States Patent
Kim et al.

(10) Patent No.: US 7,110,650 B2
(45) Date of Patent: Sep. 19, 2006

(54) METHOD FOR CONFIGURING AIR-CORE PHOTONIC-BANDGAP FIBERS FREE OF SURFACE MODES

(75) Inventors: Hyang Kyun Kim, Sunnyvale, CA (US); Shanhui Fan, Palo Alto, CA (US); Gordon S. Kino, Stanford, CA (US); Jonghwa Shin, Stanford, CA (US); Michel J. F. Digonnet, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 33 days.

(21) Appl. No.: 10/938,755

(22) Filed: Sep. 10, 2004

(65) Prior Publication Data

US 2005/0118420 A1 Jun. 2, 2005

Related U.S. Application Data

(60) Provisional application No. 60/564,896, filed on Apr. 23, 2004, provisional application No. 60/502,329, filed on Sep. 12, 2003, provisional application No. 60/502,390, filed on Sep. 12, 2003, provisional application No. 60/502,531, filed on Sep. 12, 2003.

(51) Int. Cl.
*G02B 6/20* (2006.01)
(52) U.S. Cl. ........................ 385/125; 385/123
(58) Field of Classification Search ......... 385/123–128
See application file for complete search history.

(56) References Cited

U.S. PATENT DOCUMENTS

| 4,826,434 A | 5/1989 | Krueger |
| 5,310,343 A | 5/1994 | Hasegawa et al. |
| 5,802,236 A | 9/1998 | DiGiovanni et al. |
| 6,174,167 B1 | 1/2001 | Wohrle |
| 6,243,522 B1 | 6/2001 | Allan et al. |
| 6,260,388 B1 | 7/2001 | Borrelli et al. |
| 6,334,017 B1 | 12/2001 | West |
| 6,334,019 B1 | 12/2001 | Birks et al. |

(Continued)

FOREIGN PATENT DOCUMENTS

WO    WO 99/64903 A1    12/1999

(Continued)

OTHER PUBLICATIONS

P. Kaiser et al., *Low-loss single material fibers made from pure fused silica*, The Bell System Technical Journal, vol. 53, No. 6, Jul.-Aug. 1974, pp. 1021-1039.

(Continued)

*Primary Examiner*—Kevin S. Wood
(74) *Attorney, Agent, or Firm*—Knobbe, Martens, Olson & Bear, LLP

(57) ABSTRACT

Coupling of core modes to surface modes in an air-core photonic-bandgap fiber (PBF) can cause large propagation losses. Computer simulations analyze the relationship between the geometry and the presence of surface modes in PBFs having a triangular hole pattern and identify ranges of core characteristic dimensions (e.g., radii) for which the fiber supports no surface modes (i.e., only core modes are present) over the entire wavelength range of the bandgap. In particular, for a hole spacing $\Lambda$ and a hole radius $\rho = 0.47\Lambda$, the core supports a single mode and supports no surface modes for core radii between about $0.68\Lambda$ and about $1.05\Lambda$. The existence of surface modes can be predicted simply and expediently by studying either the bulk modes alone or the geometry of the fiber without requiring a full analysis of the defect modes.

21 Claims, 19 Drawing Sheets

CORE RADIUS THAT DOES NOT
SUPPORT SURFACE MODES

U.S. PATENT DOCUMENTS

| | | | |
|---|---|---|---|
| 6,778,749 B1* | 8/2004 | Allan et al. | 385/125 |
| 6,917,741 B1 | 7/2005 | Fekety et al. | |
| 2002/0136516 A1 | 9/2002 | Allan et al. | |
| 2004/0105645 A1 | 6/2004 | Allan et al. | |
| 2005/0118420 A1 | 6/2005 | Kim et al. | |

FOREIGN PATENT DOCUMENTS

| | | |
|---|---|---|
| WO | WO 02/14946 A1 | 2/2002 |
| WO | PCT/US02/18045 | 9/2004 |
| WO | WO 2005/026783 A | 3/2005 |
| WO | PCT US2005/016004 | 5/2005 |

OTHER PUBLICATIONS

Pochi Yeh et al., *Theory of Bragg Fiber*, Journal of Optical Society of America, vol. 68, No. 9, Sep. 1978, pp. 1196-1201.

A. Yariv et al., *Optical Waves in Crystals: Propagation and Control of Laser Radiation*, John Wiley & Sons, New York, 1984, pp. 209-214.

J.D. Joannopoulos et al., *Photonic Crystals: Molding the flow of light*, Princeton University Press, Princeton, New Jersey, 1995, pp. 54-77.

M.J. Renn et al., *Laser-Guided Atoms in Hollow-Core Optical Fibers*, Physical Review Letters, vol. 75, No. 18, Oct. 30, 1995, pp. 3253-3256.

R.S. Windeler et al., *Silica-air microstructured fibers; Properties and applications*, Optical Fiber Communications Conference, San Diego, 1999, pp. FG1-1 and FG1-2.

J.C. Knight et al., *All-silica single mode optical fiber with photonic crystal cladding*, Optics Letters, vol. 21, No. 19, Oct. 1, 1996, pp. 1547-1549.

Jes Broeng et al., *Photonic Crystal Fibers: A New Class of Optical Waveguides*, Optical Fiber Technology, vol. 5, 1999, pp. 305-330.

F. Ramos-Mendieta et al., *Surface electromagnetic waves in two-dimensional photonic crystals: effect of the position of the surface plane*, Physical Review B, vol. 59, No. 23, Jun. 15, 1999, pp. 15112-15120.

R.F. Cregan et al., *Single-Mode Photonic Band Gap Guidance of Light in Air*, Science, vol. 285, Sep. 3, 1999, pp. 1537-1539.

Jes Broeng et al., *Analysis of air guiding photonic bandgap fibers*, Optics Letters, vol. 25, No. 2, Jan. 15, 2000, pp. 96-98.

Y. Xu et al., *Asymptotic analysis of Bragg fibers*, Optics Letters, vol. 25, No. 24, Dec. 15, 2000, pp. 1756-1758.

Kazunori Suzuki et al., *Ultrabroad band white light generation from a multimode photonic bandgap fiber with an air core*, Proceedings of Conference on Laser and Electro-Optics (CLEO) 2001, paper WIPD1-11, pp. 24-25.

Steven G. Johnson et al., *Block-iterative frequency-domain methods for Maxwell's equations in a planewave basis*, Optic Express, vol. 8, No. 3, Jan. 29, 2001, pp. 173-190.

M. Qiu, *Analysis of guided modes in photonic crystal fibers using the finite-difference time-domain method*, Microwave Optical Technology Letters, vol. 30, No. 5, Sep. 5, 2001, pp. 327-330.

J.A. West et al., *Photonic Crystal Fibers*, Proceedings of 27th European Conference on Optical Communications (ECOC'01—Amsterdam), Amsterdam, The Netherlands, Sep. 30-Oct. 4, 2001, paper ThA2.2, pp. 582-585.

T.P. White et al., *Confinement losses in microstructured optical fibers*, Optics Letters, vol. 26, No. 21, Nov. 1, 2001, pp. 1660-1662.

Niels Asger Mortensen, *Effective area of photonic crystal fibers*, Optics Express, vol. 10, No. 7, Apr. 8, 2002, pp. 341-348.

K. Saitoh et al., *Full-vectorial imaginary-distance beam propagation method based on finite element scheme: Application to photonic crystal fibers*, IEEE Journal of Quantum Electronics, vol. 38, No. 7, Jul. 2002, pp. 927-933.

N. Venkataraman et al., *Low loss (13 dB/km) air core photonic band-gap fibre*, Proceedings of European Conference on Optical Communication, ECOC 2002, Copenhagen, Denmark, PostDeadline Session 1, PostDeadline Paper PD1.1, Sep. 12, 2002.

D. Ferrarini et al., *Leakage properties of photonic crystal fibers*, Optics Express, vol. 10, No. 23, Nov. 18, 2002, pp. 1314-1319.

F. Benabid et al., *Particle levitation and guidance in hollow-core photonic crystal fiber*, Optics Express, vol. 10, No. 21, Oct. 21, 2002, pp. 1195-1203.

Wah Tung Lau et al., *Creating large bandwidth line defects by embedding dielectric waveguides into photonic crystal slabs*, Applied Physics Letters, vol. 81, No. 21, Nov. 18, 2002, pp. 3915-3917.

Burak Temelkuran et al., *Wavelength-scalable hollow optical fibres with large photonic bandgaps for $CO_2$ laser transmission*, Nature, vol. 420, Dec. 12, 2002, pp. 650-653.

T.P Hansen et al., *Air-guidance over 345m large-core photonic bandgap fiber*, Optical Fiber Communication Conference OFC'03, Post Deadline paper (Atlanta, Georgia, Mar. 2003), 3 pages.

Douglas C. Allan et al., *Surface modes and loss in air-core photonic band-gap fibers*, in Photonic Crystals Materials and Devices, A. Adibi et al. (eds.), Proceedings of SPIE, vol. 5000, 2003, pp. 161-174.

Philip Russell, *Photonic Crystal Fibers*, Science, vol. 299, Jan. 17, 2003, pp. 358-362.

B. Kuhlmey et al., *Chromatic dispersion and losses of microstructured optical fibers*, Applied Optics, vol. 42, No. 4, Feb. 1, 2003, pp. 634-639.

K. Saitoh et al., *Chromatic dispersion control in photonic crystal fibers: application to ultra-flattened dispersion*, Optics Express, vol. 11, No. 8, Apr. 21, 2003, pp. 843-852.

W. Zhi et al., *Supercell lattice method for photonic crystal fibers*, Optics Express, vol. 11, No. 9, May 5, 2003, pp. 980-991.

Dimitri G. Ouzounov et al., *Dispersion and nonlinear propagation in air-core photonic band-gap fibers*, Proceedings of Conference on Laser and Electro-Optics (CLEO) 2003, Baltimore, USA, Jun. 1-6, 2003, paper CThV5, 2 pages.

Dirk Müller et al., *Measurement of Photonic Band-gap Fiber Transmission from 1.0 to 3.0 μm and Impact of Surface Mode Coupling*, Proceedings of Conference on Laser and Electro-Optics (CLEO) 2003, Baltimore, USA, Jun. 1-6, 2003, paper QTuL2, 2 pages.

G. Renversez et al., *Dispersion management with microstructured optical fibers: ultraflattened chromatic dispersion with low losses*, Optics Letters, vol. 28, No. 12, Jun. 15, 2003, pp. 989-991.

G. Bouwmans et al., *Properties of a hollow-core photonic bandgap fiber at 850 nm wavelength*, Optics Express, Jul. 14, 2003, vol. 11, No. 14, pp. 1613-1620.

Charlene M. Smith et al., *Low-loss hollow-core silica/air photonic bandgap fibre*, Nature, vol. 424, No. 6949, Aug. 7, 2003, pp. 657-659.

Jonathan C. Knight, *Photonic crystal fibres*, Nature, vol. 424, No. 6950, Aug. 14, 2003, pp. 847-851.

J.M. Pottage et al., *Robust photonic band gaps for hollow core guidance in PCF made from high index glass*, Optics Express, vol. 11, No. 22, Nov. 3, 2003, pp. 2854-2861.

K. Saitoh et al., *Leakage loss and group velocity dispersion in air-core photonic bandgap fibers*, Optics Express, vol. 11, No. 23, Nov. 17, 2003, pp. 3100-3109.

Theis P. Hansen et al., *Air-Guiding Photonic Bandgap Fibers: Spectral Properties, Macrobending Loss, and Practical Handling*, Journal of Lightwave Technology, vol. 22, No. 1, Jan. 2004, pp. 11-15.

K. Saitoh et al., *Air-core photonic band-gap fibers: the impact of surface modes*, Optics Express, vol. 12, No. 3, Feb. 9, 2004, pp. 394-400.

B.J. Mangan et al., *Low loss (1.7 dB/km) hollow core photonic bandgap fiber*, Conference on Optical Fiber Communication OFC 2004, Post Deadline paper PDP24, Los Angeles, California, Feb. 22-27, 2004, 3 pages.

J.A. West et al., *Surface modes in air-core photonic band-gap fibers*, Optics Express, vol. 12, No. 8, Apr. 19, 2004, pp. 1485-1496.

H.K. Kim et al., *Designing air-core photonic-bandgap fibers free of surface modes*, IEEE Journal of Quantum Electronics, vol. 40, No. 5, May 2004, pp. 551-556.

M.J.F. Digonnet et al., *Simple geometric criterion to predict the existence of surface modes in air-core photonic-bandgap fibers*, Optics Express, vol. 12, No. 9, May 3, 2004, pp. 1864-1872.

Blazephotonics, *HC—1550—02 Hollow Core Photonic Bandgap Fiber*, 4 pages.

* cited by examiner

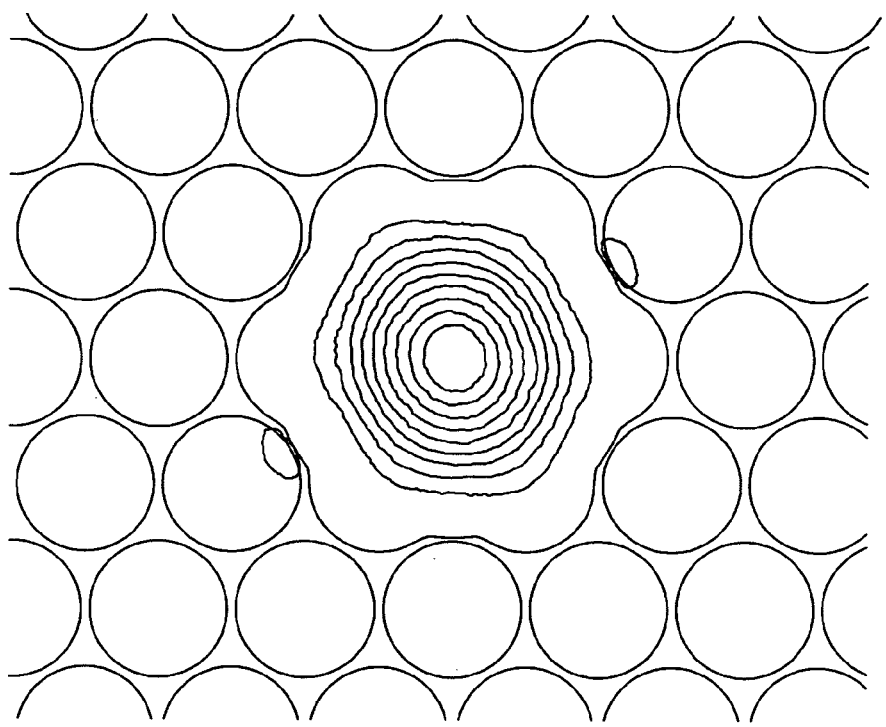
*FIG. 4* Fundamental Core Mode
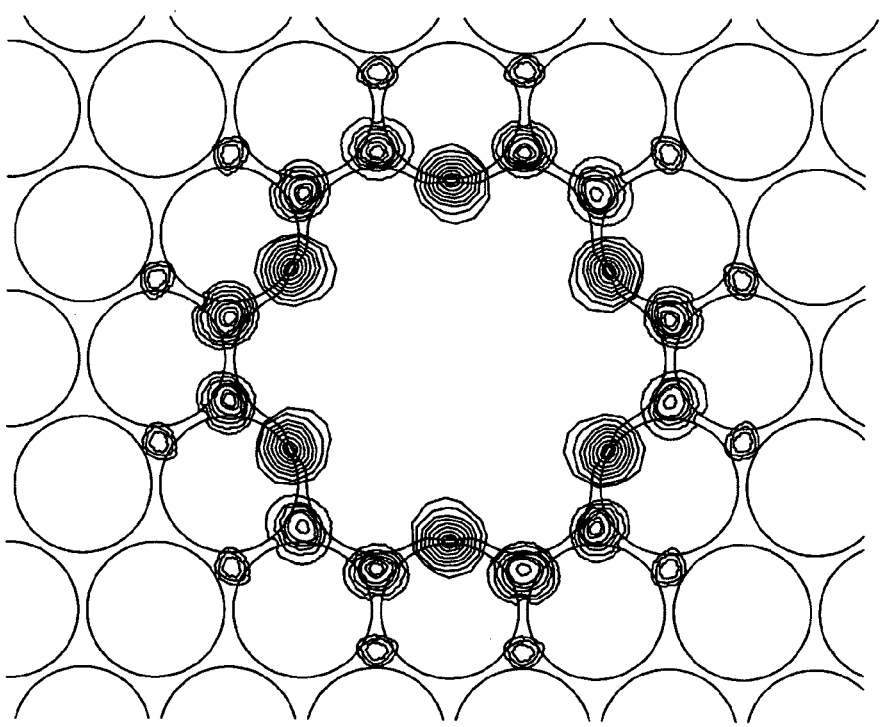
*FIG. 3* Surface Modes

Bulk Mode

R=0.9Λ

R=1.2Λ

R=2.1Λ

CORE RADIUS THAT DOES NOT
SUPPORT SURFACE MODES

CORE RADIUS THAT
SUPPORTS SURFACE MODES

Contour: 0.1 step from 0.1 to 0.9

METHOD FOR CONFIGURING AIR-CORE PHOTONIC-BANDGAP FIBERS FREE OF SURFACE MODES

RELATED APPLICATIONS

The present application claims the benefit of priority under 35 U.S.C. § 119(e) of U.S. Provisional Application No. 60/502,329, filed on Sep. 12, 2003; U.S. Provisional Application No. 60/502,390, filed on Sep. 12, 2003; U.S. Provisional Application No. 60/502,531, filed on Sep. 12, 2003; and U.S. Provisional Application No. 60/564,896, filed on Apr. 23, 2004, which are incorporated by reference herein.

BACKGROUND OF THE INVENTION

1. Field of the Invention

The present application is in the field of optical fibers for propagating light, and more particularly is in the field of photonic-bandgap fibers having a hollow core, or a core with a refractive index lower than the cladding materials.

2. Description of the Related Art

Air-core photonic-bandgap fibers (PBFs) have attracted great interest in recent years due to their unique advantages over conventional fibers. In particular, the propagation loss in an air-core PBF is not limited by the core material, and it is expected that the propagation loss can be exceedingly low. The nonlinear effects in an air-core PBF are very small, and the core can be filled with liquids or gases to generate the desired light-matter interaction. Numerous new applications enabled by these advantages have been demonstrated recently. Such applications are described, for example, in Burak Temelkuran et al., *Wavelength-scalable hollow optical fibres with large photonic bandgaps for $CO_2$ laser transmission*, Nature, Vol. 420, 12 Dec. 2002, pages 650–653; Dimitri G. Ouzounov et al., *Dispersion and nonlinear propagation in air-core photonic band-gap fibers*, Proceedings of Conference on Laser and Electro-Optics (CLEO) 2003, Baltimore, USA, 1–6 Jun. 2003, paper CThV5, 2 pages; M. J. Renn et al., *Laser-Guided Atoms in Hollow-Core Optical Fibers*, Physical Review Letters, Vol. 75, No. 18, 30 Oct. 1995, pages 3253–3256; F. Benabid et al., *Particle levitation and guidance in hollow-core photonic crystal fiber*, Optics Express, Vol. 10, No. 21, 21 Oct. 2002, pages 1195–1203; and Kazunori Suzuki et al., *Ultrabroad band white light generation from a multimode photonic bandgap fiber with an air core*, Proceedings of Conference on Laser and Electro-Optics (CLEO) 2001, paper WIPD1–11, pages 24–25, which are hereby incorporated herein by reference.

Calculations of selected properties of the fundamental mode of the PBFs have also been reported in, for example, R. F. Cregan et al., *Single-Mode Photonic Band Gap Guidance of Light in Air*, Science, Vol. 285, 3 Sep. 1999, pages 1537–1539; Jes Broeng et al., *Analysis of air guiding photonic bandgap fibers*, Optics Letters, Vol. 25, No. 2, Jan. 15, 2000, pages 96–98; and Jes Broeng et al., *Photonic Crystal Fibers: A New Class of Optical Waveguides*, Optical Fiber Technology, Vol. 5, 1999, pages 305–330, which are hereby incorporated herein by reference.

Surface modes, which do not exist in conventional fibers, are defect modes that form at the boundary between the air core and the photonic-crystal cladding. Surface modes can occur when an infinite photonic crystal is abruptly terminated, as happens for example at the edges of a crystal of finite dimensions. Terminations introduce a new set of boundary conditions, which result in the creation of surface modes that satisfy these conditions and are localized at the termination. See, for example, F. Ramos-Mendieta et al., *Surface electromagnetic waves in two-dimensional photonic crystals: effect of the position of the surface plane*, Physical Review B, Vol. 59, No. 23, 15 Jun. 1999, pages 15112–15120, which is hereby incorporated herein by reference. In a photonic crystal, the existence of surface modes depends strongly on the location of the termination. See, for example, A. Yariv et al., *Optical Waves in Crystals: Propagation and Control of Laser Radiation*, John Wiley & Sons, New York, 1984, pages 209–214, particularly at page 210; and J. D. Joannopoulos et al., *Photonic Crystals: Molding the flow of light*, Princeton University Press, Princeton, N.J., 1995, pages 54–77, particularly at page 73; which are hereby incorporated herein by reference; and also see, for example, F. Ramos-Mendieta et al., *Surface electromagnetic waves in two-dimensional photonic crystals: effect of the position of the surface plane*, cited above. For example, in photonic crystals made of dielectric rods in air, surface modes are induced only when the termination cuts through rods. A termination that cuts only through air is too weak to induce surface modes. See, for example, J. D. Joannopoulos et al., *Photonic Crystals: Molding the flow of light*, cited above.

Recent demonstrations have shown that surface modes play a particularly important role in air-core PBFs, and mounting evidence indicates that surface modes impose serious limitations in air-core photonic-bandgap fibers See, for example, Douglas C. Allan et al., *Surface modes and loss in air-core photonic band-gap fibers*, in Photonic Crystals Materials and Devices, A. Adibi et al. (eds.), Proceedings of SPIE, Vol. 5000, 2003, pages 161–174; Wah Tung Lau et al., *Creating large bandwidth line defects by embedding dielectric waveguides into photonic crystal slabs*, Applied Physics Letters, Vol. 81, No. 21, 18 Nov. 2002, pages 3915–3917; and Dirk Müller et al., *Measurement of Photonic Band-gap Fiber Transmission from 1.0 to 3.0 µm and Impact of Surface Mode Coupling*, Proceedings of Conference on Laser and Electro-Optics(CLEO) 2003, Baltimore, USA, 1–6 June 2003, paper QTuL2, 2 pages, which are hereby incorporated herein by reference, and also see, for example, J. D. Joannopoulos et al., *Photonic Crystals: Molding the flow of light*, cited above; A. Yariv et al., *Optical Waves in Crystals: Propagation and Control of Laser Radiation*, cited above; and F. Ramos-Mendieta et al., *Surface electromagnetic waves in two-dimensional photonic crystals: effect of the position of the surface plane*, cited above. Unless suitably designed, a fiber will support many surface modes.

In contrast to surface modes, a core mode (e.g., a fundamental core mode) is one in which the peak of the mode intensity is located in the core. In most cases, most of the energy will also be contained within the air core. The propagation constants of surface modes often fall close to or can even be equal to the propagation constant of the fundamental core mode. See, for example, Dirk Müller et al., *Measurement of Photonic Band-gap Fiber Transmission from 1.0 to 3.0 µm and Impact of Surface Mode Coupling*, cited above. Strong experimental and analytical evidence indicates that the fundamental core mode couples to one or more of these surface modes. Such coupling may be caused, for example, by random perturbations in the fiber cross-section. Since surface modes are inherently lossy due to their high energy density in the dielectric of the fiber, such coupling is a source of propagation loss. Furthermore, since surface modes occur across the entire bandgap, no portion of the available spectrum is immune to this loss mechanism. Recent findings have demonstrated that surface modes are a cause of the reduced transmission bandwidth in a 13-dB/km air-core PBF manufactured by Corning. See, for example, N. Venkataraman et al., *Low loss (13 dB/km) air core photonic band-gap fibre*, Proceedings of European Conference on Optical Communication, ECOC 2002, Copenhagen, Denmark, PostDeadline Session 1, PostDeadline Paper PD1.1, Sep. 12, 2002; and C. M. Smith, et al., *Low-loss hollow-core silica/air photonic bandgap fibre*, Nature, Vol. 424, No. 6949, 7 Aug. 2003, pages 657–659, which are incorporated by reference herein. This effect is believed to be the source of the remaining loss (approximately 13 dB/km) in this air-core photonic-bandgap fiber. See, for example, Douglas C. Allan et al, *Photonic Crystals Materials and Devices*, cited above. Understanding the physical origin of surface modes and identifying fiber configurations that are free of such modes across the entire bandgap is therefore of importance in the ongoing search for low-loss PBFs.

SUMMARY OF THE INVENTION

The embodiments disclosed herein are based on information obtained in an investigation of the properties of the core modes and the surface modes of PBFs using numerical simulations. The investigation focused on the most common PBF geometry, namely fibers with a periodic, triangular pattern of cylindrical air-holes in the cladding and a circular core obtained by introducing an air defect. Such fibers are described, for example, in R. F. Cregan et al., *Single-Mode Photonic Band Gap Guidance of Light in Air*, cited above; Jes Broeng et al., *Analysis of air-guiding photonic bandgap fibers*, cited above; and Jes Broeng et al., *Photonic Crystal Fibers: A new class of optical waveguides*, Optical Fiber Technology, cited above. The results are also applicable to a broad range of air-hole patterns (e.g., hexagonal patterns, square patterns, etc.), hole shapes, and core shapes. The results are also applicable to other photonic-bandgap fibers, namely, fiber with similar geometries that operate on the same photonic-bandgap principle but with a core not necessarily filled with air (e.g., a core filled with another gas, a vacuum, a liquid, or a solid), with cladding holes not necessarily filled with air (e.g., cladding holes filled with another gas, a vacuum, a liquid, or a solid), and with solid portions of the cladding not necessarily made of silica (e.g., the cladding may comprise another solid or a multiplicity of solids). As used herein, hole or a core that is not filled with a solid or a liquid is referred to herein as being hollow. It is understood here that the respective refractive indices of the materials that make up the core, the cladding holes, and the solid portion of the cladding should be selected such that the fiber structure supports a guided mode via the photonic-bandgap effect. This implies that the refractive index of the core and the refractive index of the holes should be lower than that of the refractive index of the solid portions of the cladding, and that the difference between these indices should be large enough.

New geometries are proposed herein for air-core fibers or fibers with a core that has a lower refractive index than the solid portions of the cladding. These geometries have ranges of core characteristic dimensions (e.g., core radii when the core is circular) for which the fiber core supports no surface modes over the entire wavelength range of the bandgap, and only core modes are present. In particular, for a circular core with a radius between about 0.7Λ and about 1.05Λ, where Λ is the hole-to-hole spacing of the triangular pattern, the core in a proposed new geometry supports a single mode and does not support any surface modes. The absence of surface modes suggests that fibers within this range of configuration should exhibit substantially lower losses than current fibers. As further shown below, the existence of surface modes in the defect structure can be readily predicted either from a study of the bulk modes alone or even more simply by a straightforward geometric argument. Because the structure is truly periodic, prediction of the existence of surface modes in accordance with the methods described below is quicker and less complicated than a full analysis of the defect modes.

The methods disclosed herein can be used to predict whether a particular fiber geometry will support surface modes so that fibers can be designed and manufactured that do not support surface modes. In particular, as illustrated below in the detailed description, the presence of surface modes can be avoided by selecting the core radius or other characteristic dimension such that the edge of the core does not cut through any of the circles inscribed in the veins (e.g., the solid intersection regions) of the PBF lattice. The technique works for broad ranges of geometries and hole sizes.

In order to avoid surface modes, the techniques described herein are used to design the core shape such that the core does not intersect any of the veins of the PBF lattice (e.g., the core intersects only the segments that join the veins of the PBF lattice). By following this general criterion, PBFs can be designed to be free of surface modes.

An aspect in accordance with embodiments of the invention is a method of making a photonic-bandgap fiber. The method uses a photonic-bandgap fiber that comprises a material with a pattern of regions formed therein to form a photonic crystal lattice. The material has a first refractive index. The pattern of regions has a second refractive index lower than the first refractive index. The method comprises determining intensity profiles of a highest frequency bulk mode proximate to the regions. The method forms a central core in the photonic crystal lattice. The core has an edge that intersects the pattern of regions at locations where the intensities of the highest frequency bulk mode are low enough that the fiber supports no surface modes. Preferably, the regions in the material are circular; and the pattern of regions is periodic and arranged such that each group of three adjacent regions forms a triangle with a respective first portion of the material between each pair of regions and with a respective second portion of the material forming a central area within each group of three adjacent regions. The central core is formed in the photonic crystal lattice such that the edge of the central core passes only through the first portions of the material. In particular embodiments, the regions in the material are holes that have walls defined by the surrounding material. Advantageously, the holes in the material are hollow. The holes in the material may be filled with air, gas or liquid having the second refractive index. Alternatively, the circular regions comprise a solid having the second refractive index. In certain embodiments, the material is a dielectric, such as, for example, silica.

Another aspect in accordance with an embodiment of the invention is a photonic-bandgap fiber that comprises a photonic crystal lattice. The lattice comprises a first material having a first refractive index. The first material has a pattern of a second material formed therein. The second material has a second refractive index lower than the first refractive index. The photonic crystal lattice has a plurality of first regions that support intensity lobes of the highest frequency bulk mode and has a plurality of second regions that do not support intensity lobes of the highest frequency bulk mode. A central core is formed in the photonic crystal lattice. The central core has an edge that passes only through the second regions of the dielectric lattice. Preferably, the pattern of the second material is periodic and comprises a plurality of geometric regions. Each geometric region has a respective center, and adjacent geometric regions are spaced apart by a center-to-center distance $\Lambda$. Each geometric region of the second material is circular and has a radius $\rho$, wherein the radius $\rho$ is less than $0.5\Lambda$. Preferably, the pattern is triangular, and the first regions comprise circles inscribed between three adjacent geometric regions. In certain embodiments, each inscribed circle has a radius a equal to $(\Lambda/\sqrt{3})-\rho$. Also, preferably, the radius $\rho$ of each geometric region is approximately $0.47\Lambda$. In certain embodiments, the core is generally circular, and the edge of the core has a radius within one of a plurality of ranges of radii. A first of the plurality of ranges of core radii extends from a radius of approximately $0.68\Lambda$ to a radius of approximately $1.05\Lambda$. A second of the plurality of ranges of core radii extends from a radius of approximately $1.26\Lambda$ to a radius of approximately $1.43\Lambda$. A third of the plurality of ranges of core radii extends from a radius of approximately $1.64\Lambda$ to a radius of approximately $1.97\Lambda$. In particularly preferred embodiments, the first of the plurality of ranges of core radii extends from a radius of approximately $0.685\Lambda$ to a radius of approximately $1.047\Lambda$, the second of the plurality of ranges of core radii extends from a radius of approximately $1.262\Lambda$ to a radius of approximately $1.420\Lambda$, and the third of the plurality of ranges of core radii extends from a radius of approximately $1.635\Lambda$ to a radius of approximately $1.974\ \Lambda$.

Another aspect in accordance with embodiments of the invention is a geometric method for selecting the dimensions of a core for producing a photonic-bandgap fiber free of surface modes. The photonic-bandgap fiber has a photonic crystal lattice comprising a first material having a first refractive index. The material encompasses a periodic pattern of regions of a second material. The second material has a second refractive index lower than the first refractive index. Each region of the second material is spaced apart from an adjacent region of the second material by a membrane of the first material and each intersection of membranes forms a vein of the first material. The method comprises defining an inscribed central area within each vein of the second material such that an outer periphery of the inscribed central area is tangential to the outer peripheries of the adjacent regions around the vein. The method further comprises defining a plurality of ranges of core characteristic dimensions wherein any core having a dimension within one of the plurality of ranges has an edge that does not pass through any of the inscribed central areas. The method further comprises selecting a core having a dimension within one of the plurality of ranges of core characteristic dimensions. Preferably, each region has a respective center, and adjacent regions are spaced apart by a center-to-center distance $\Lambda$. Also preferably, each region of the second material is circular and has a radius $\rho$, and the radius $\rho$ is less than $0.5\Lambda$. In certain embodiments, the pattern is triangular, and the inscribed central area circular. Preferably, the circle has a radius $\alpha$ equal to $(\Lambda/\sqrt{3})-\rho$. In particular embodiments, the radius $\rho$ of each region is approximately $0.47\Lambda$. In such embodiments, the characteristic dimension of the core is the radius of a circle, and a first of the plurality of ranges of core characteristic dimensions extends from a radius of approximately $0.68\Lambda$ to a radius of approximately $1.05\Lambda$, a second of the plurality of ranges of core characteristic dimensions extends from a radius of approximately $1.26\Lambda$ to a radius of approximately $1.43\Lambda$, and a third of the plurality of ranges of core characteristic dimensions extends from a radius of approximately $1.64\Lambda$ to a radius of approximately $1.97\Lambda$. In particularly preferred embodiments, the first of the plurality of ranges of core characteristic dimensions extends from a radius of approximately $0.685\Lambda$ to a radius of approximately $1.047\Lambda$, the second of the plurality of ranges of core characteristic dimensions extends from a radius of approximately $1.262\Lambda$ to a radius of approximately $1.420\Lambda$, and the third of the plurality of ranges of core characteristic dimensions extends from a radius of approximately $1.635\Lambda$ to a radius of approximately $1.974\ \Lambda$.

Another aspect in accordance with embodiments of the invention is a photonic-bandgap fiber that supports no surface modes. The photonic-bandgap fiber comprises a photonic crystal lattice region comprising a material having a first refractive index. The material has a periodic pattern of regions formed therein. Each region has a second refractive index lower than the first refractive index. Each region is spaced apart from an adjacent region by a membrane of the material. Each group of adjacent regions is formed around a central area of the material. The central area within each group of adjacent regions is defined by an inscribed circle having a circumference tangential to the circumferences of the adjacent regions. A core is formed in the photonic-bandgap fiber. The core has a characteristic dimension selected such that the edge of the core passes only through portions of the material that are not within any of the inscribed circles in the central areas. Preferably, the material is a dielectric material, such as, for example, silica. Also, preferably, the pattern is triangular and each group of adjacent regions comprises three regions. In particularly preferred embodiments, the core is generally circular, and the characteristic dimension is the radius of the core.

Another aspect in accordance with embodiments of the invention is a method for producing a photonic-bandgap fiber that does not support surface modes. The method comprises selecting a photonic-bandgap fiber having a photonic crystal lattice that comprises a material having a first refractive index. The material has a periodic triangular pattern of regions formed therein. Each region has a refractive index lower than the first refractive index. The material comprises first areas between adjacent holes and comprises second areas between only two adjacent holes. The second areas interconnect the first areas. The method further comprises forming a core in the photonic crystal lattice. The core has a characteristic dimension selected such that the edge of the core intersects only the second areas of the photonic crystal region. Preferably, the material is a dielectric material, such as, for example, silica. Also preferably, the pattern is triangular, and each group of adjacent regions comprises three regions. In particularly preferred embodiments, the core is generally circular, and the characteristic dimension is the radius of the core.

BRIEF DESCRIPTION OF THE DRAWINGS

Embodiments in accordance with the present invention are described below in connection with the accompanying drawing figures in which:

FIG. 3 illustrates contour lines that represent equal intensity lines of a typical surface mode for the air-core PBF of FIG. 1;

FIG. 4 illustrates contour lines that represent equal intensity lines of the fundamental core mode for the air-core PBF of FIG. 1;

DETAILED DESCRIPTION OF THE PREFERRED EMBODIMENT

The following description is based on a photonic bandgap fiber (PBF) with a cladding photonic crystal region comprising a triangular lattice comprising a plurality of circular holes filled with a gas (e.g., air) in silica or other solids, where the holes are spaced apart by a period Λ. Silica-based PBFs are described, for example, in R. F. Cregan et al., *Single-Mode Photonic Band Gap Guidance of Light in Air*, cited above; Jes Broeng et al., *Analysis of air-guiding photonic bandgap fibers*, cited above; and Jes Broeng et al., *Photonic Crystal Fibers: A New Class of Optical Waveguides*, cited above. For simplicity, such fibers are referred to herein as air-hole fibers; however, as discussed above, the following discussions and results are also applicable to photonic-bandgap fibers with a core and/or all or some of the cladding holes filled with other materials besides air (e.g., another gas, a vacuum, a liquid, or a solid) and with solid portions of the cladding made of materials other than silica (e.g., a different solid or a multiplicity of solids). Furthermore, the results are also adaptable to other patterns of holes (e.g., hexagonal patterns, square patterns, etc.).

Figure 1:
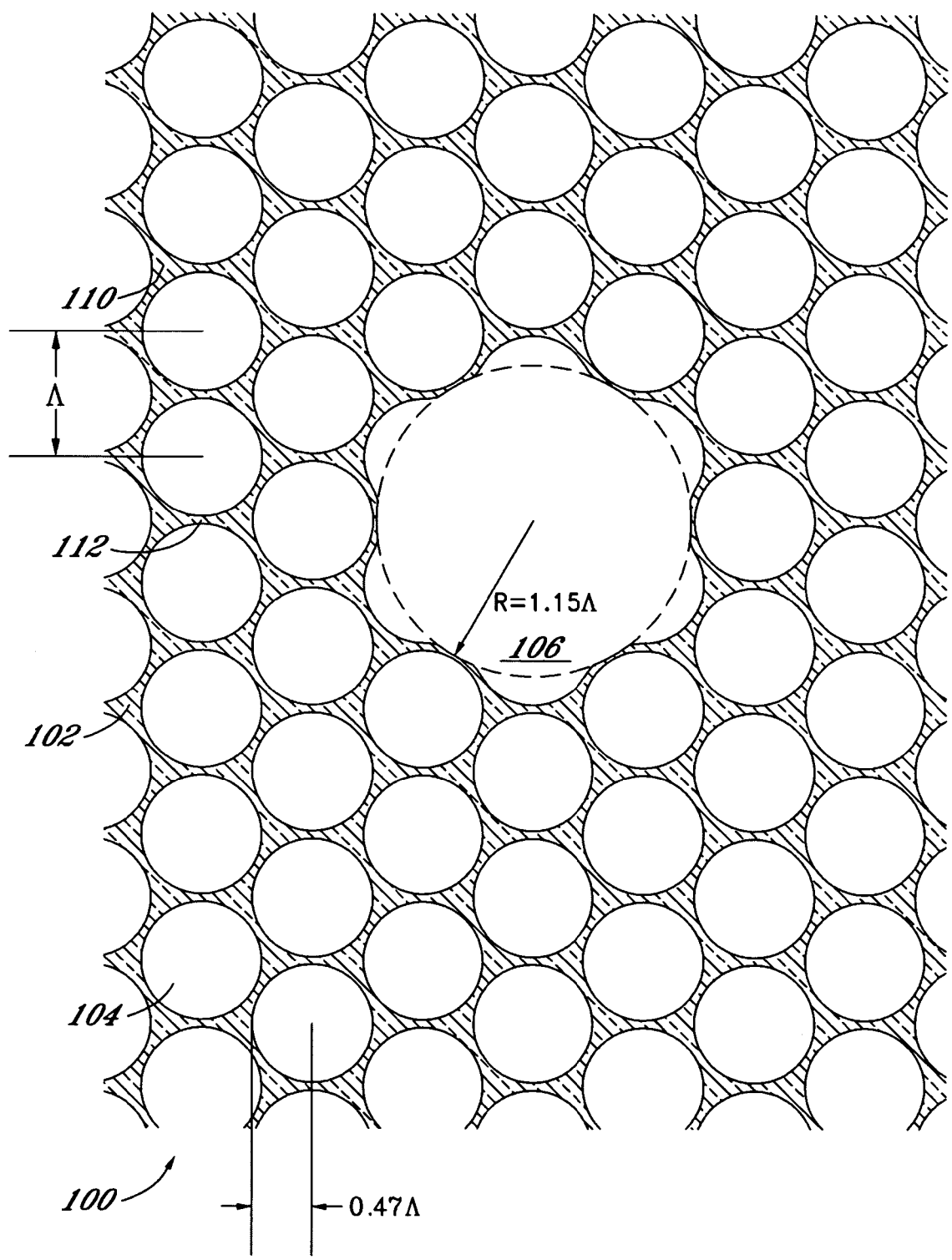
FIG. 1 illustrates a partial cross section of an exemplary triangular-pattern air-core photonic-bandgap fiber (PBF) for a core radius of $1.15\Lambda$ and a hole radius $\rho$ of approximately $0.47\ \Lambda$.

A partial cross section of an exemplary triangular-pattern air-core PBF 100 is illustrated in FIG. 1. As illustrated, the fiber 100 comprises a solid dielectric lattice 102 comprising a plurality of air holes 104 surrounding an air core 106. Three exemplary adjacent holes 104 are shown in more detail in FIG. 2. The portion of the solid lattice 102 between any three adjacent holes 104 is referred to as a vein (or a corner) 110, and the thinner regions connecting two adjacent veins (i.e., a region between any two adjacent holes) is referred to as a segment (or a membrane) 112. In the illustrated embodiment, each air hole 104 has a radius ρ. The center-to-center spacing of adjacent air holes 104 is referred to as the period Λ of the photonic crystal.

As will be discussed in more detail below, each vein 110 can be approximated by an inscribed circle 114 of radius a, wherein the circumference of the inscribed circle 114 is tangential to the circumferences of three holes 104 surrounding the vein 110. Simple geometric calculations readily show that the radius α of the inscribed circle 114 is related to the radius ρ and the period Λ of the air holes 104 as follows:

$$a = (\Lambda/\sqrt{3}) - \rho$$

As illustrated in FIG. 1, the air-core 106 of the PBF 100 is advantageously created by introducing a larger cylindrical air hole of radius R at the center of the fiber. The location of this cylinder, reproduced in FIG. 1 as a dashed circle, is referred to herein as the edge of the core 106. The radius R is referred to herein as the characteristic dimension of the air-core 106. In the example of the circular core illustrated in FIG. 1, the radius R is the radius of the circular core The following discussion is adaptable to cores having other shapes and characteristic dimensions (e.g., the shortest distance from the center to the nearest boundary of a polygonal-shaped core). In the PBF 100 of FIGS. 1 and 2, the radius R is selected to be 1.1Λ, and the radius ρ of each air hole 104 is selected to be 0.47Λ. For example, the air-core 106 of radius 1.15Λ is advantageously selected because the core radius corresponds to a core formed in practice by removing seven cylinders from the center of the PBF preform (e.g., effectively removing the glass structure between the seven cylinders). Such a configuration is commonly used and is described, for example, in J. A. West et al., *Photonic Crystal Fibers, Proceedings of 27th European Conference on Optical Communications (ECOC'01—Amsterdam)*, Amsterdam, The Netherlands, Sep. 30-Oct. 4, 2001 paper ThA2.2, pages 582–585, which is hereby incorporated herein by reference.

Figure 2:
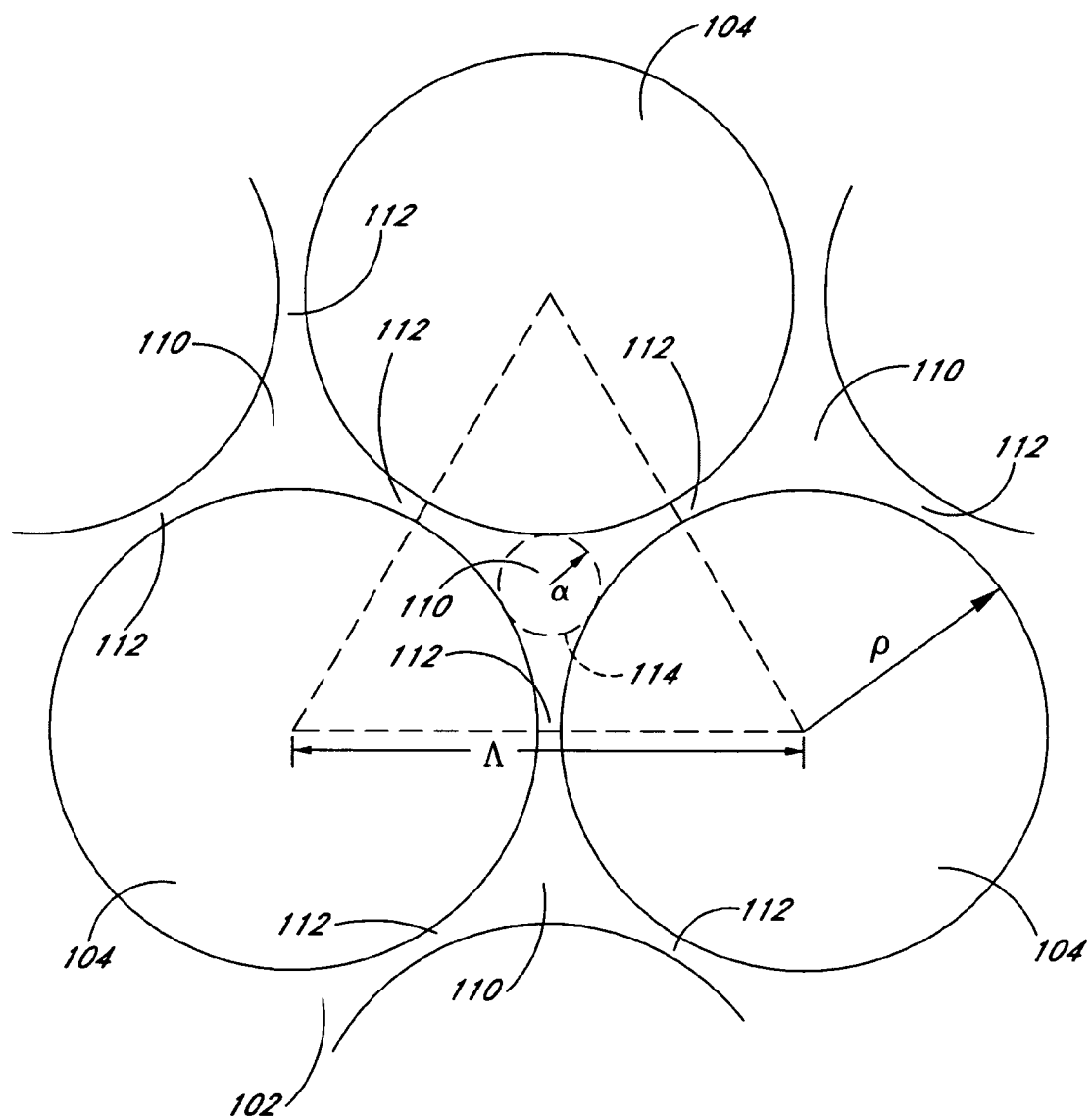
FIG. 2 illustrates an enlarged view of the partial cross section of FIG. 1 to provide additional detail on the spatial relationships between the air holes, the segments (membranes) between adjacent air holes and the veins (corners) at the intersections of the segments.

As discussed above, surface modes are defect modes that form at the boundary between the core 106 and the photonic-crystal cladding 102. A typical surface mode for the triangular-pattern air-core PBF 100 of FIGS. 1 and 2 is illustrated in FIG. 3. A typical fundamental core mode for the PDF 100 of FIGS. 1 and 2 is illustrated in FIG. 4. In FIGS. 3 and 4, the contour lines represent equal intensity lines. The outmost intensity line in each group has a normalized intensity of 0.1 and the innermost intensity line has a normalized intensity of 0.9, and each intervening intensity line represents a normalized step increase of 0.1.

Figure 5:
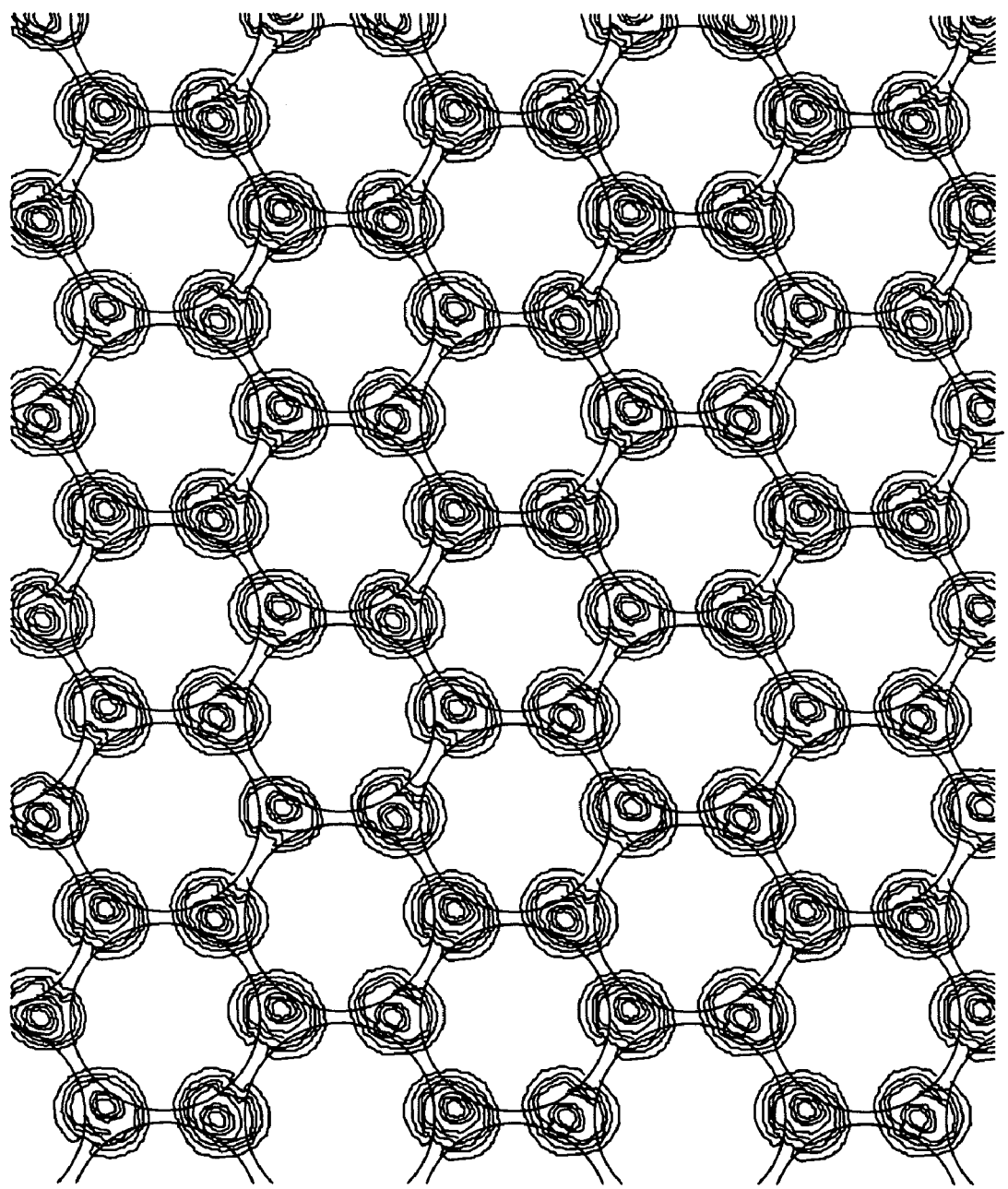
FIG. 5 illustrates contour lines that represent equal intensity lines of a typical bulk mode for the triangular-pattern air-core PBF of FIG. 1, but without the removal of the central structure to form the air core 106.

In the absence of a core, a PBF carries only bulk modes. An example of bulk mode is illustrated in FIG. 5. The bulk mode of FIG. 5 is calculated for the same triangular-pattern air-core PBF 100 illustrated in FIG. 1, but without the removal of the central structure to form the air core 106. As in FIGS. 3 and 4, the contour lines in FIG. 5 represent equal intensity lines.

The particular bulk mode illustrated in FIG. 5 comprises a series of narrow intensity lobes centered on each of the thicker dielectric corners 110 of the photonic crystal 102. Other bulk modes may have different lobe distributions (e.g., all the lobes may be centered on membranes 112 rather than on corners 110).

As discussed above, a fiber will support many surface modes unless the fiber is suitably designed to eliminate all surface modes. As further discussed above, the propagation constants of the surface modes are often close to or equal to the propagation constant of the fundamental core mode, and, as a result, the core mode can easily be coupled to the surface modes (e.g., by random perturbations in the fiber cross section), which results in an increased propagation loss for the fundamental core mode. This problem is also present for other core modes besides the fundamental mode when the fiber is not single mode.

By varying the radius R of the air core 106, the effect of the core radius on the core modes and the effect of surface truncation on the surface mode behavior can be systematically studied. One such study is based on simulations performed on the University of Michigan AMD Linux cluster of parallel Athlon 2000MP processors using a full-vectorial plane-wave expansion method. An exemplary full-vectorial plane wave expansion method is described, for example, in Steven G. Johnson et al., *Block-iterative frequency-domain methods for Maxwell's equations in a plane-wave basis*, Optic Express, Vol. 8, No. 3, 29 Jan. 2001, pages 173–190, which is hereby incorporated herein by reference.

The simulations use a grid resolution of Λ/16 and a supercell size of 8 Λ×8Λ. The solid portion of the cladding was assumed to be silica, and all holes were assumed to be circular and filled with air. When running the simulations with 16 parallel processors, complete modeling of the electric-field distributions and dispersion curves of all the core modes and surface modes of a given fiber typically takes between 7 hours and 10 hours.

The results of the simulation for a triangular pattern indicate that a photonic bandgap suitable for air guiding exists only for air-hole radii ρ larger than about 0.43Λ. The largest circular air-hole radius that can be fabricated in practice (e.g., so that sufficient silica remains in the membranes 112 between adjacent air holes 104 to provide a supporting structure) is slightly higher than 0.49Λ. In the study, a structure is simulated that has an air-hole radius ρ between these two extreme values. In particular, ρ is selected to be approximately 0.5Λ. Although the simulations described herein are carried out for p=0.47Λ, similar results have been obtained for any value of ρ between 0.43Λ to 0.5Λ, and the qualitative conclusions described herein are valid for any air-hole size in the range of 0.43Λ to 0.5 Λ.

Figure 6:
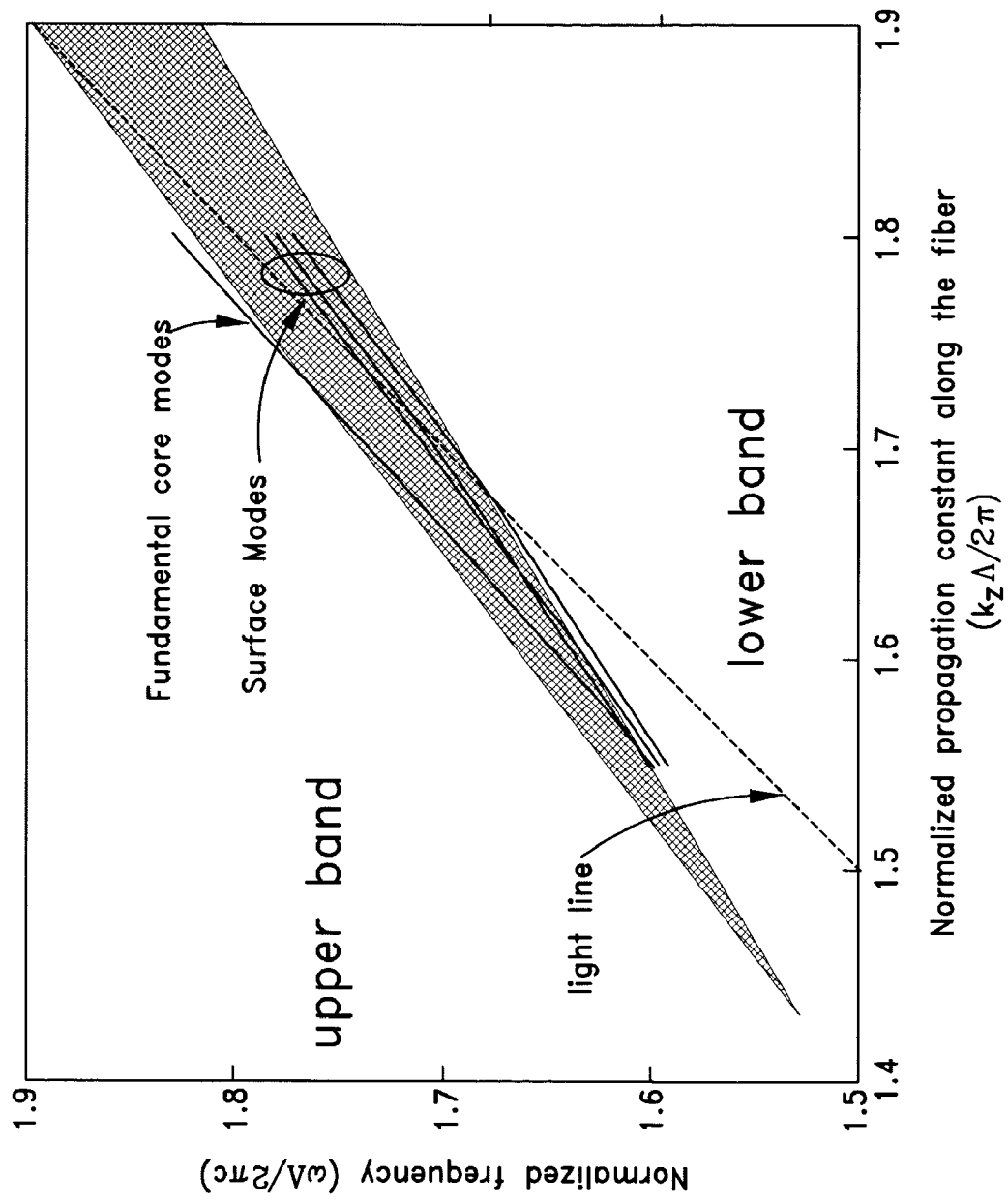
FIG. 6 illustrates dispersion curves of the defect modes for the air-core photonic-bandgap fiber (PBF) of FIG. 1 having a triangular-pattern of holes with a photonic-crystal structure of period (i.e., hole-to-hole spacing) Λ and a hole radius ρ of approximately 0.47Λ, surrounding an air-core having a radius R of approximately 1.15Λ, wherein the shaded (cross hatched) area represents the photonic bandgap of the crystal.

FIG. 6 illustrates the theoretical ω-$k_z$ diagram of the fiber geometry under study generated for a core radius R=1.15Λ (see, for example, FIG. 1). In FIG. 6, the vertical axis is the optical angular frequency ω=2πc/λ normalized to 2πc/Λ (i.e., Λ/λ), where λ is the free-space wavelength of the light signal, c is the velocity of light in vacuum, and Λ is the photonic-crystal structure period. Thus, the vertical axis represents ωΛ/2πc=Λ/λ, which is a dimensionless quantity. The horizontal axis in FIG. 6 is the propagation constant along the axis of the fiber (z direction) $k_z$, normalized to 2π/Λ (i.e., $k_z$Λ/2π).

The first photonic bandgap supported by the infinite structure of the simulated fiber 100 of FIG. 1 is represented by the shaded (cross-hatched) region. The size and shape of the first photonic bandgap depends on the value of the radii π of the air holes 104 (which are equal to 0.47Λ in the illustrated simulation), but the bandgap is very nearly independent of the dimension of the core 106. The dashed line in FIG. 6 represents the light line, below which no core modes can exist, irrespective of the core size and the core shape. The portion of the shaded region above the dashed line shows that in the simulated fiber 100, the normalized frequencies for which light can be guided in the air core range from approximately 1.53 to approximately 1.9.

The solid curves in FIG. 6 represent the dispersion relations of the core mode and the surface modes. The air core actually carries two fundamental modes. Each mode is nearly linearly polarized, and the polarization of each mode is orthogonal to the polarization of the other mode. These two modes are very nearly degenerate. In other words, the two modes have almost exactly the same dispersion curve within the bandgap. The topmost curve in FIG. 6 actually comprises two dispersion curves, one for each of these two fundamental modes; however, the two curves are so nearly identical that they cannot be distinguished on this graph. The related intensity profiles of selected modes at $k_z$Λ/2π=1.7 are plotted in FIG. 4 for one of the two fundamental core modes and in FIG. 3 for an exemplary surface mode. These profiles indicate that the highest-frequency modes inside the bandgap are the two fundamental core modes. All other modes in the bandgap are surface modes, which have their intensities localized at the core-cladding boundary, as shown in FIG. 3. The strength of the spatial overlap with the silica portions of the fiber is different for core and surface modes. The difference in strength results in the core mode having a group velocity close to c and the surface modes having a lower group velocity, as illustrated in FIG. 6.

FIG. 6 also illustrates another distinguishing feature of the core and surface modes. In particular, the curves for the surface modes always cross the light line within the bandgap. In contrast, the curves for the core modes never cross the light line within the bandgap.

Figure 7:
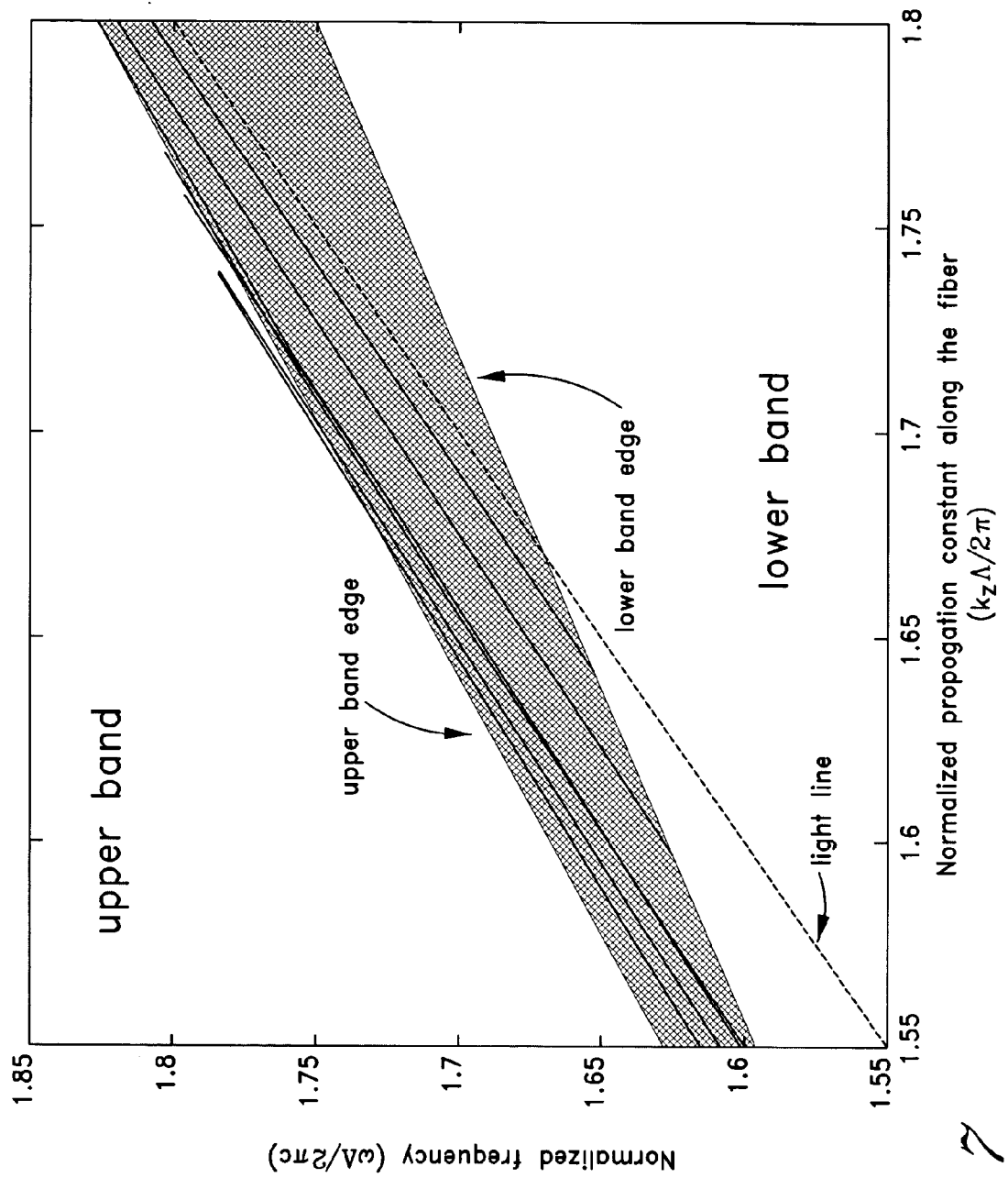
FIG. 7 illustrates dispersion curves of the defect modes for an air-core PBF having a core radius R of approximately 1.8 Λ.
Figure 8:
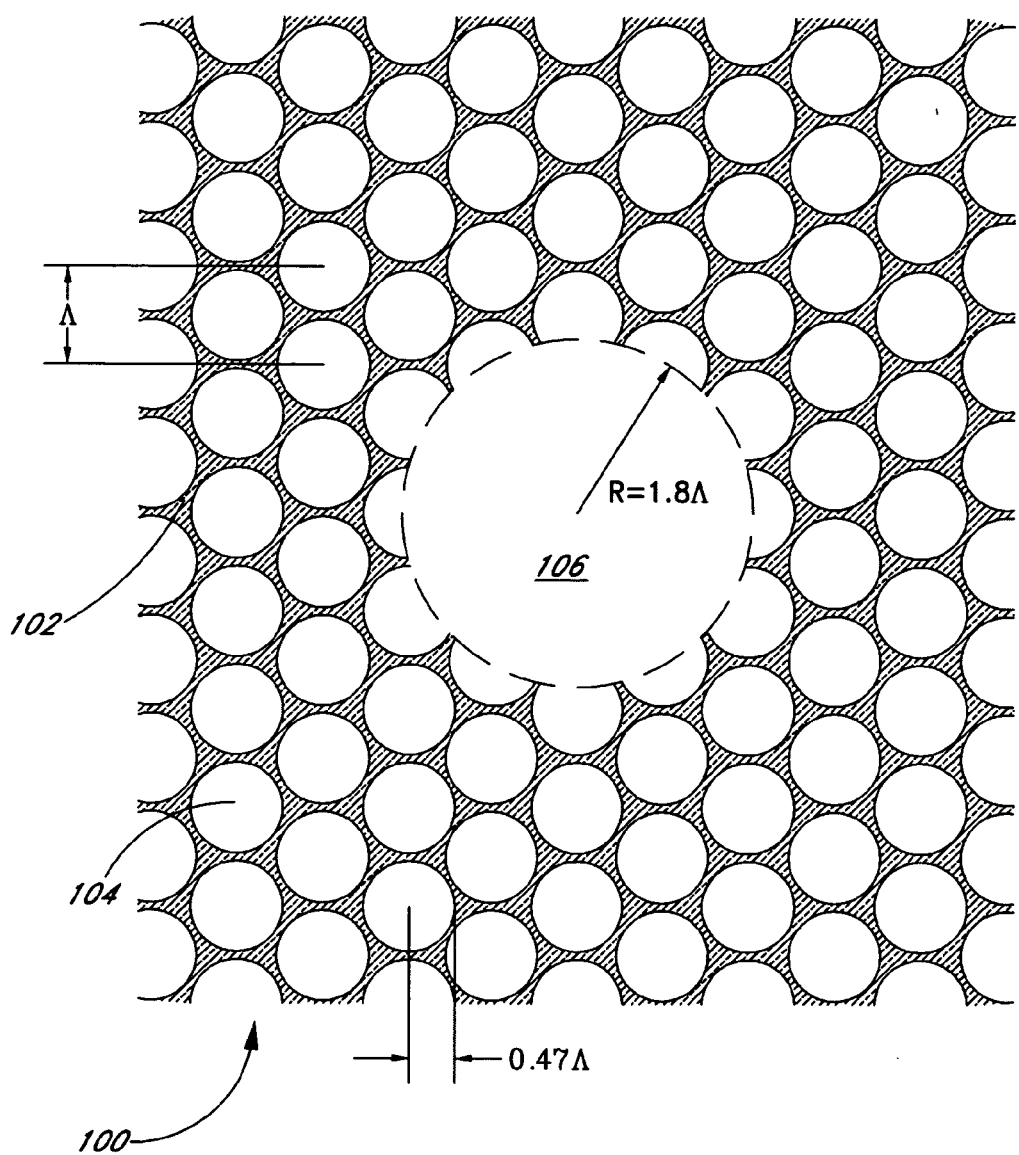
FIG. 8 illustrates a partial cross section showing the hole pattern and air-core shape of a PBF from which the dispersion curves of FIG. 7 are obtained.

The behaviors of the core mode and the surface modes are investigated as a function of defect size by changing the core radius R from 0.6Λ to 2.2Λ in 0.1Λ steps. FIG. 7 illustrates the ω-$k_z$ diagram generated for the same fiber geometry as used to generate the information in FIG. 6, but for a larger core radius (R=1.8Λ). As illustrated by the partial fiber cross section in FIG. 8, the larger core radius is formed, for example, by removing additional lattice structure beyond the central seven cylinders of the preform so that the surface of the core 106 intersects the thinner membranes 112 between the holes 104 rather than intersecting the thicker dielectric corners 110. As expected, the number of core modes appearing in FIG. 7 for the embodiment of FIG. 8 is greater than for the embodiment of FIG. 1. In addition, all the modes are core modes for this larger radius. As the frequency is increased from the low-frequency cutoff of the bandgap, the highest order core modes appear first, in a group of four or more modes (e.g., four in FIG. 7). This feature depends on the core size and mode degeneracy. See, for example Jes Broeng et al., *Analysis of air-guiding photonic bandgap fibers*, cited above. As the frequency is further increased, the number of modes reaches some maximum number (14 in the example illustrated in FIG. 7) at a normalized frequency (ωΛ/2πc) of approximately 1.7. Above a normalized frequency of approximately 1.7, the number of modes gradually decreases to two (the two fundamental modes) at the high-frequency cutoff of the bandgap. The maximum number of core modes occurs at or in the vicinity of the frequency where the light line intersects the lower band edge. In the embodiment illustrated by the plot in FIG. 7, the light line intersects the lower band edge at a normalized frequency (ωΛ/2πc) having a value of around 1.67. Note that in FIG. 7, many of the curves represent multiple modes that are degenerate and thus overlap in the diagram.

Figure 9:
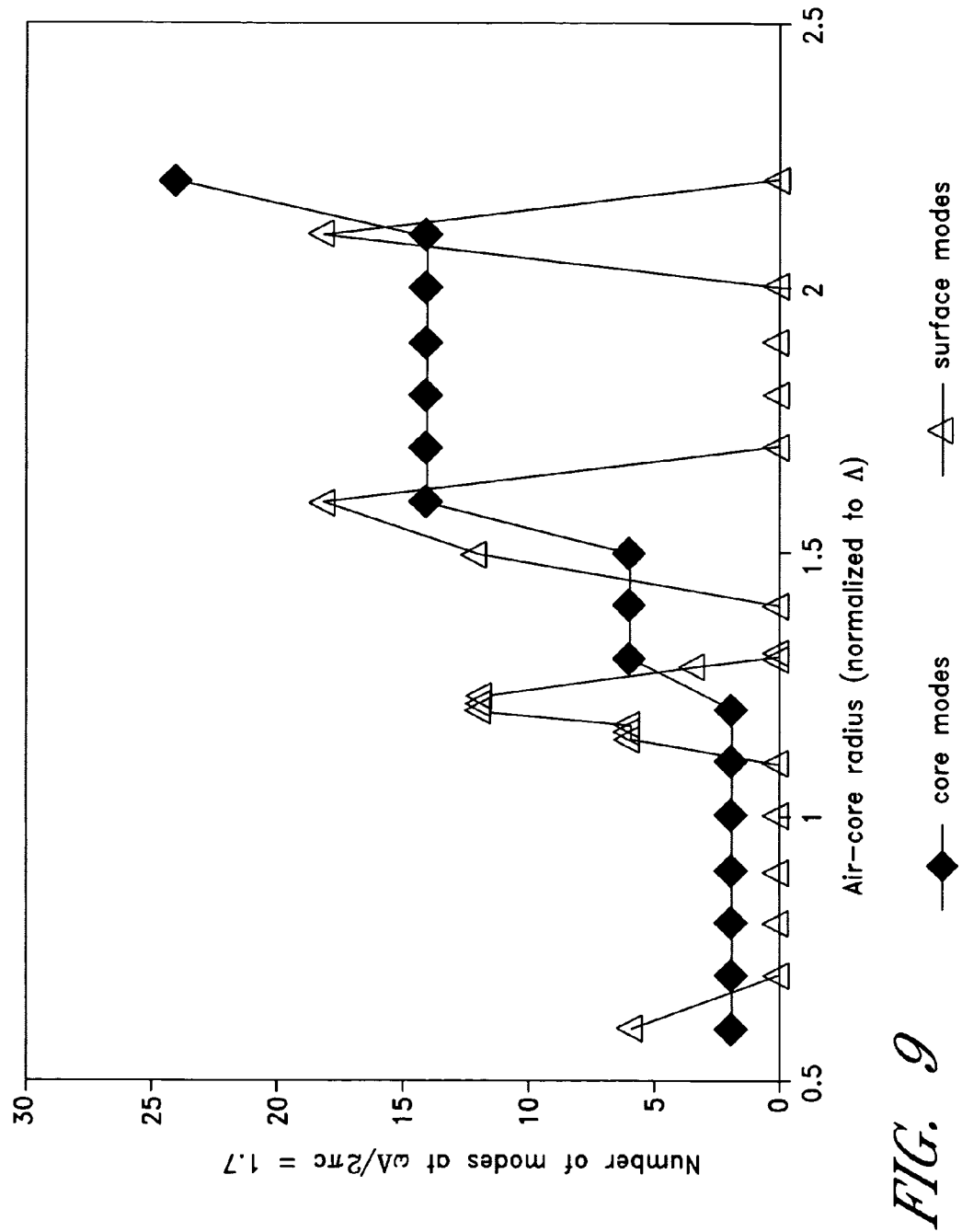
FIG. 9 illustrates a graph of the number of core modes (diamonds) and surface modes (triangles) versus the air-core radius at the normalized frequency $\omega\Lambda/2\pi c = 1.7$.
Figure 10A:
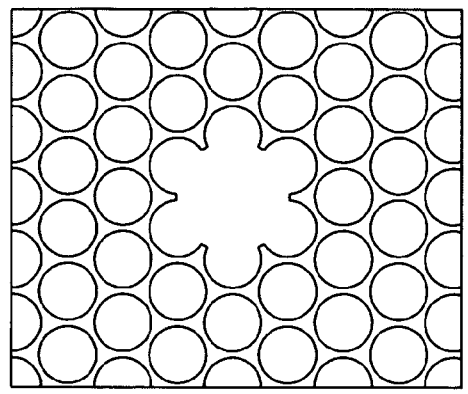
FIGS. 10A, 10B and 10C illustrate the core shapes for core radii of 0.9 Λ, 1.2Λ, and 2.1Λ, respectively, from which the information in FIG. 9 was derived.
Figure 10B:
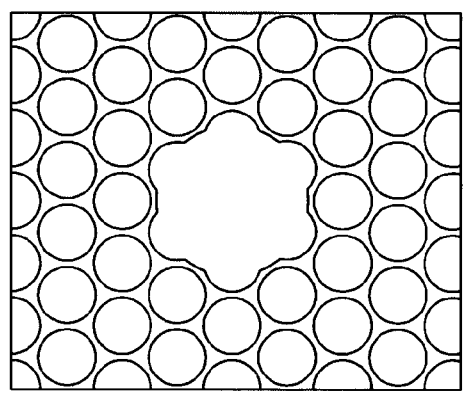
Figure 10C:
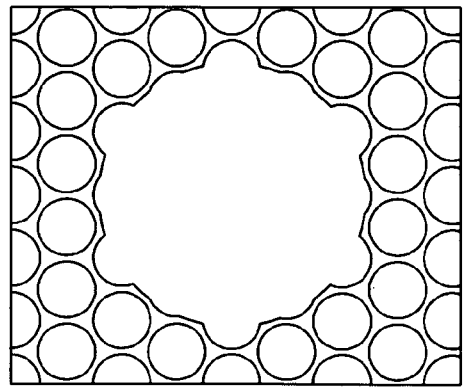

FIG. 9 illustrates the dependence of this maximum number of core modes (i.e., the number of modes is plotted at ωΛ/2πc=1.7) on R. The number of surface modes is also shown in FIG. 9. In addition, core shapes for representative radii of R=0.9Λ, R=1.2Λ, and R=2.1Λ are illustrated in FIG. 10A, FIG. 10B and FIG. 10C, respectively. As stated above, the grid resolution used to generate the data points in FIG. 9 was Λ/16. However, to generate additional points in the more interesting range of core radii between 1.1Λ and 1.3Λ, the grid size was reduced to Λ/32 in that range. As a result, the absolute number of surface modes predicted in this range does not scale the same way as in the rest of the graph. This is inconsequential since the primary interest in generating the data points is to determine the boundaries of the surface mode regions.

The behaviors of the core modes in PBFs and in conventional fibers based on total internal reflection have striking similarities. The fundamental mode, like an $LP_{01}$ mode, is doubly degenerate (see FIGS. 6 and 7), is very nearly linearly polarized, and exhibits a Gaussian-like intensity profile. See, for example, Jes Broeng et al., *Analysis of air-guiding photonic bandgap fibers*, cited above. The next four modes are also degenerate, and the electric field distributions of these four modes are very similar to those of the $HE_{21}^{odd}$, $HE_{21}^{even}$, $TE_{01}$, and $TM_{01}$ modes of conventional fibers. Many of the core modes, especially the low-order modes, exhibit a two-fold degeneracy in polarization over much of the bandgap. As the core radius is increased, the number of core modes increases in discrete steps (see FIG. 9), from two (the two fundamental modes) to six (these two modes plus the four degenerate modes mentioned above), then 14 (because the next eight modes happen to reach cutoff at almost the same radius), etc.

FIG. 9 also illustrates another aspect of the modes. In particular, when R falls in certain bounded ranges, all modes are found to be core modes. The first three of the bounded ranges are:

range 1 from approximately 0.7Λ to approximately 1.1 Λ;

range 2 from approximately 1.3Λ to approximately 1.4Λ; and range 3 from approximately 1.7Λ to approximately 2.0 Λ.

Figure 11:
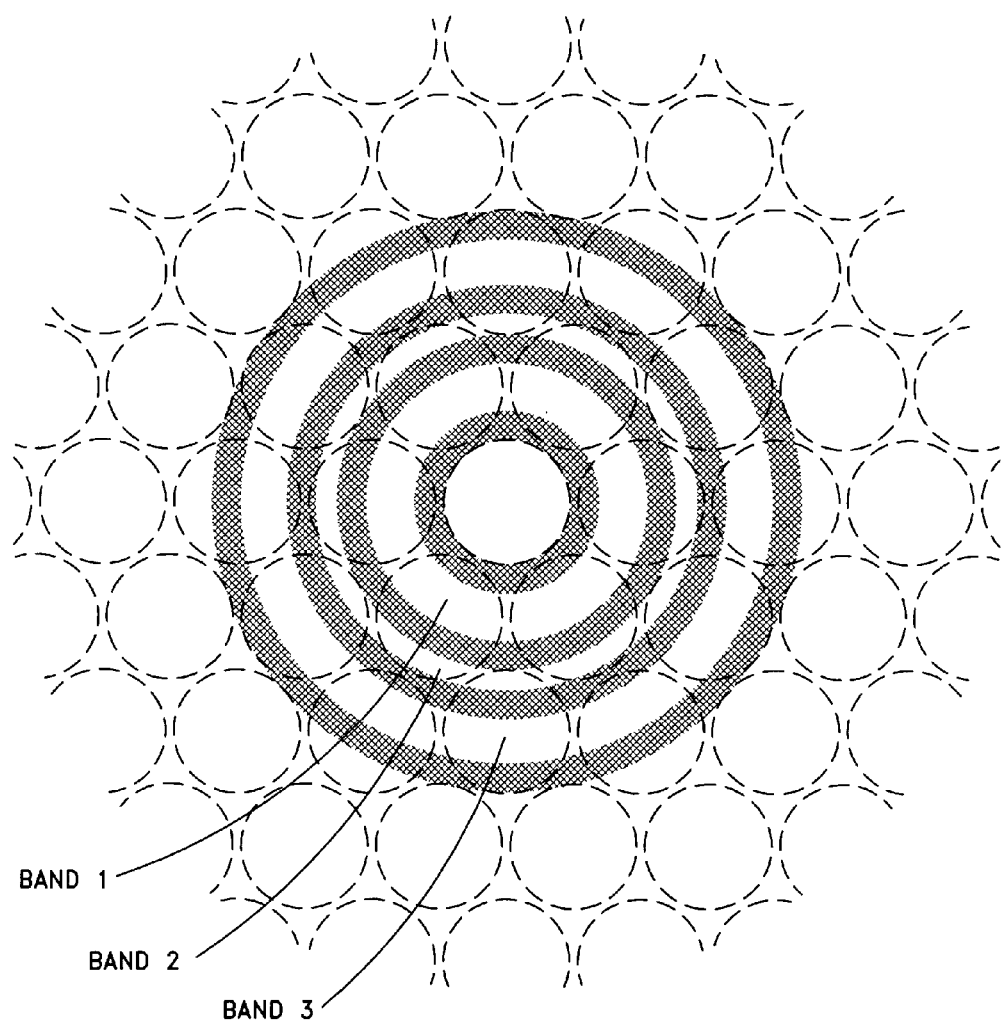
FIG. 11 illustrates a graphical representation of the air-core radius ranges that support core modes only (unshaded rings) and both core and surface modes (shaded rings.

FIG. 7 illustrates the case where R is equal to 1.8Λ, which is one particular example of a surface-mode-free PBF in range 3. The surface-mode-free ranges determined by the computer simulation are illustrated schematically in FIG. 11. In FIG. 11, the background pattern of circles represents the infinite photonic crystal structure, the four shaded (cross hatched) annular areas represent the ranges of core radii that support surface modes, and the three unshaded annular areas (labeled as band 1, band 2 and band 3) represent the first three ranges of radii that are free of surface modes. Note that for radii less than 0.5Λ (e.g., the central unshaded portion of FIG. 11), the core does not support core modes that are guided by the photonic-bandgap effect.

FIG. 11 is simply a different way to graph the regions of no surface modes shown in FIG. 9. Thus, the three ranges of radii in FIG. 9 that support no surface modes, as shown by the open triangles that fall along the bottom horizontal axis, are graphed as the three white annular (unshaded) regions in FIG. 11 (bands 1, 2 and 3). The complementary (shaded) bands between the white bands correspond to the ranges of radii in FIG. 9 where the triangles are above the horizontal axis and thus represent radii that support surface modes.

In the first of the unshaded ranges in FIG. 11 (e.g., band 1 from approximately 0.7Λ to approximately 1.1Λ), the core supports a single core mode and does not support any surface modes at all across the entire wavelength range of the bandgap, i.e., the PBF is truly single mode. There do not appear to be any previous reports of a single-mode all-silica PBF design in the literature. Note that in band 2, band 3 and all other bands representing larger radii, the fiber is no longer single mode.

An example of a terminating surface shape that falls in this single-mode range (e.g., range 1) is shown in FIG. 10A for R equal to 0.9Λ. These particular configurations may be fabricated using small tips of glass protruding into the core using an extrusion method and other known fabrication techniques.

The number of surface modes is also strongly dependent on the core radius, albeit in a highly non-monotonic fashion. For core radii in the vicinities of approximately 0.6Λ, approximately 1.2Λ, approximately 1.6Λ, and approximately 2.1Λ, many surface modes are introduced, resulting in the peaks in the number of surface modes. The peaks are apparent in FIG. 9. Moreover, in these vicinities, the number of surface modes varies rapidly with R. Typical experimental PBFs are fabricated by removing the central 7 cylinders (R approximately equal to 1.15Λ) or 19 cylinders (R approximately equal to 2.1Λ) from the preform to form the core 106; however, these particular values of R, which happen to be more straightforward to manufacture, also happen to lead to geometries that support surface modes, as shown, for example, in FIG. 9.

Based on the foregoing results of the computer simulations, the basic conditions at which surface modes occur have been investigated and new structures are proposed that have no surface modes. The basic conditions lead to the observation that surface modes are created when the surface of the core 106 intersects one or more of the dielectric corners 110 of the photonic crystal lattice 102. From this observation, a fast and simple geometric criterion is obtained for evaluating whether a particular fiber configuration supports surface modes. As discussed below, when the geometric criterion is applied to triangular-pattern PBFs 100 with a circular air core 106, the approximate geometric model yields quantitative predictions in acceptable agreement with the results of computer simulations described above.

As discussed above, surface modes can occur when an infinite photonic crystal is abruptly terminated, as happens for example at the edges of a crystal of finite dimensions. For example, in photonic crystals made of dielectric rods in air, surface modes are induced only when the termination cuts through rods. A termination that cuts only through air is too weak to induce surface modes.

In an air-core PBF 100, the core 106 also acts as a defect that perturbs the crystal lattice 102 and may introduce surface modes at the edge of the core 106. Whether surface modes appear, and how many appear, depends on how the photonic crystal is terminated, which determines the magnitude of the perturbation introduced by the defect. In the absence of an air core, a PBF carries only bulk modes, as discussed above with respect to FIG. 5.

When the air core 106 is introduced as shown in FIGS. 1, 3 and 4, the core 106 locally replaces the dielectric material of the crystal lattice 102 with air. The portions of the surface of the core 106 that cut through the cladding air holes 104 in FIG. 1 replace air by air. Thus, just as in the case of a planar photonic crystal (as described, for example, in J. D. Joannopoulos et al., *Photonic Crystals: Molding the flow of light*, cited above), those portions of the core surface do not induce significant perturbation. Only the portions of the core surface that cut through the dielectric corners 110 or the dielectric membrane 112 of the crystal lattice 102 in FIG. 1 replace dielectric by air and thereby perturb the bulk modes of FIG. 5. Whether the perturbation is sufficient to potentially induce surface modes, such as the surface modes shown in FIG. 3, is discussed below.

Since a core 106 of any size and shape always cuts through some dielectric material, some perturbation is always introduced by the core 106. The sign of the perturbation is such that in the ω-k diagram, the bulk modes are all shifted up in frequency from their frequencies in their respective unperturbed positions. For a silica/air PBF 100, the perturbation is comparatively weak, and the frequency shift is small such that almost all perturbed bulk modes remain in a bulk mode band. Exceptions to the foregoing are modes from the highest frequency bulk-mode band of the lower band (referred to hereinafter as "HFBM"). Because such modes are located just below the bandgap in the ω-k diagram, the perturbation moves them into the bandgap as surface modes. See, for example, J. D. Joannopoulos et al., *Photonic Crystals: Molding the flow of light*, cited above.

Figure 13:
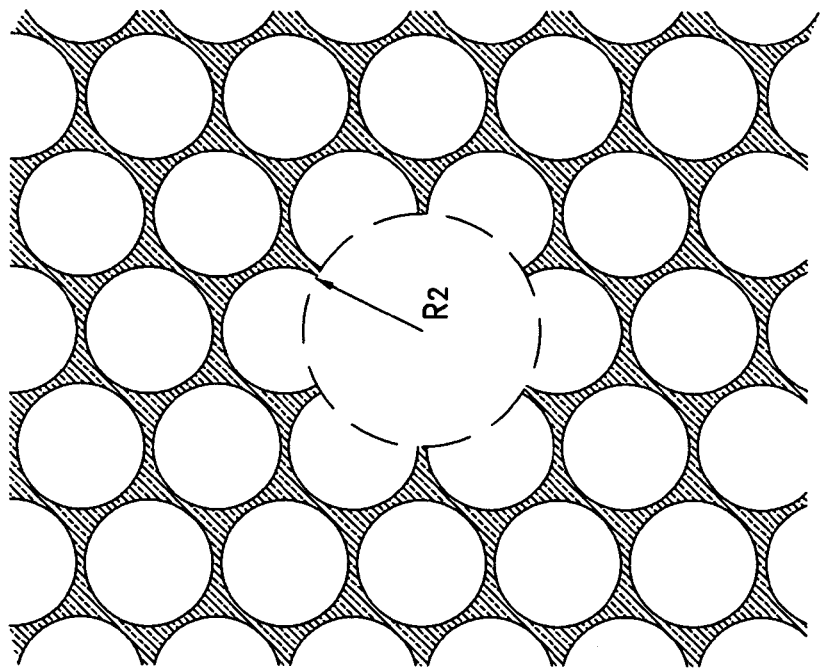
FIG. 13 illustrates the partial cross section of the triangular-pattern air-core PBF of FIG. 1 with a core of radius $R_2$ formed in the photonic crystal lattice, wherein the surface of the core does not intersect the corners of the crystal lattice and wherein surface modes are not supported.
Figure 12:
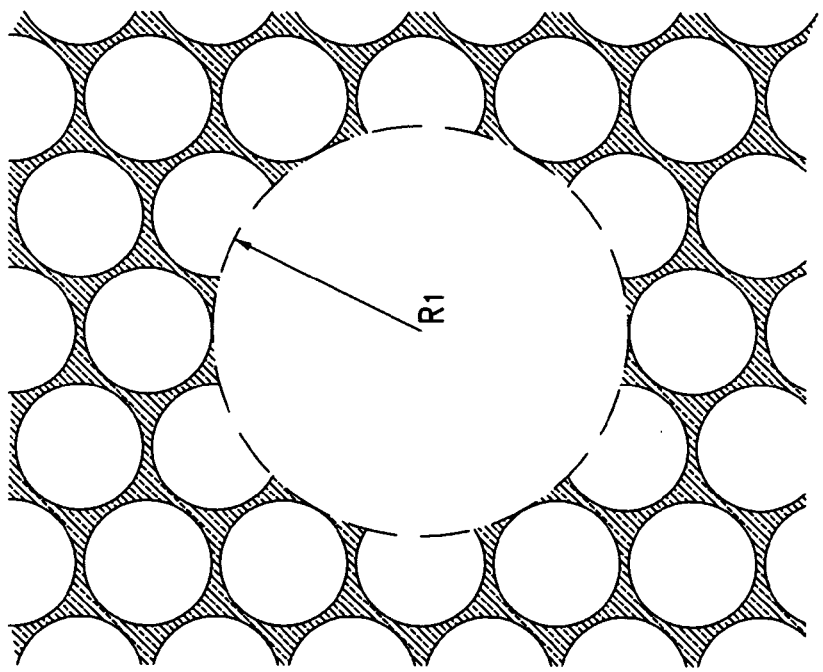
FIG. 12 illustrates the partial cross section of the triangular-pattern air-core PBF of FIG. 1 with a core of radius $R_1$ formed in the photonic crystal lattice, wherein the surface of the core intersects the corners of the crystal lattice and wherein surface modes are supported.

Surface modes can always be written as an expansion of bulk modes. For the weak perturbation considered here, it can be shown that the main term in this expansion is the HFBM, as expected in view of the origin of these surface modes. The HFBM is the bulk mode illustrated in FIG. 5. As illustrated in FIG. 5, the lobes of the mode are all centered on corners 110 of the crystal 102, which results in two important consequences. First, because surface modes are induced by a perturbation of this bulk mode, the lobes of the surface modes are also centered on the corners 110, as shown, for example, in FIG. 3. Second, for the HFBM to be perturbed and yield surface modes, the perturbation must occur in dielectric regions of the photonic crystal lattice 102 that carry a sizable HFBM intensity, e.g., in regions at the corners 110 of the photonic crystal 102. These observations show that surface modes are strongly correlated with the magnitude of the perturbation introduced by the air core 106 on the HFBM. If the surface of the core 106 intersects lobes of the HFBM at the corners 110 of the dielectric lattice 102 (as illustrated, for example, by a core of radius $R_1$ in FIG. 12), the perturbation is large and surface modes are induced. The number of surface modes then scales like the highest intensity intersected by the core 106 in the dielectric 102. Conversely, if the surface of the core 106 does not intersect any of the lobes of this bulk mode (as illustrated, for example, by a core of radius $R_2$ in FIG. 13), no surface modes are created.

Figure 14:
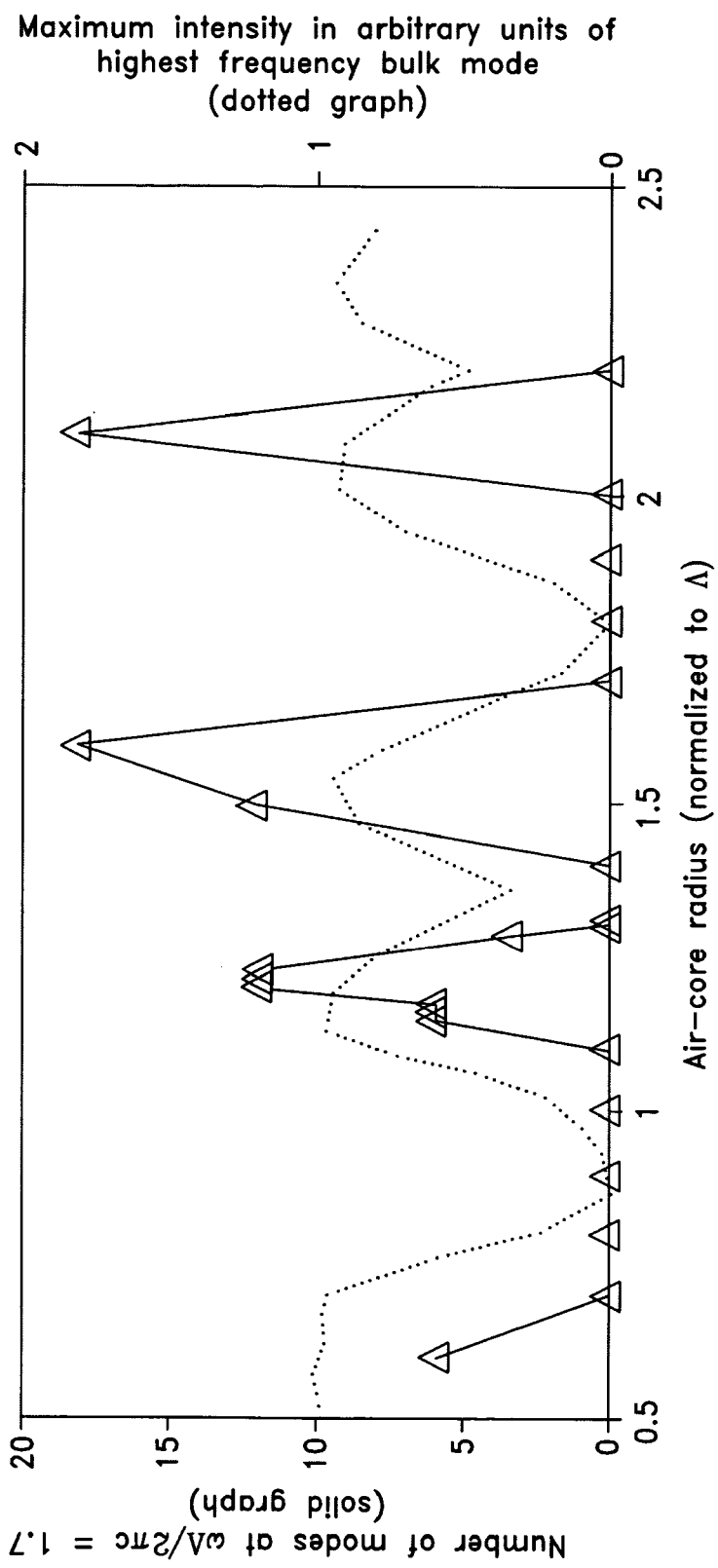
FIG. 14 illustrates a plot (dotted curve) of the maximum intensity of the highest frequency bulk mode on a circle of radius R as a function of R overlaid on the plot (solid curve) of the maximum number of surface modes as a function of R from FIG. 9.

The foregoing is illustrated in FIG. 14, which reproduces the plot of the number (values on the left vertical axis) of surface modes at $\omega\Lambda/2\pi c=1.7$ on a circle of radius R as a function of R normalized to $\Lambda$ (horizontal axis) as a solid curve. FIG. 14 also includes a plot (dotted curve) of the maximum intensity (values in arbitrary units on the right vertical axis) of the highest frequency bulk mode. FIG. 14 clearly shows the relationship between the maximum intensity and the number of surface modes. The two curves in FIG. 14 are clearly strongly correlated, which confirms that surface modes occur for radii R such that the edge of the core cuts through high-intensity lobes of the highest frequency bulk mode. Based on this principle, a first approximate dependence of the number of surface modes on the core radius was developed. By comparison to the results of exact simulations, the foregoing shows that the results obtained using this HFBM criterion predicts thee presence or absence of surface modes fairly accurately. Of course, many other kinds of perturbations can induce surface modes in the photonic crystal 102, so that the foregoing condition for the absence of surface modes is a necessary condition but it is not always a sufficient condition.

In one criterion for determining the presence of the surface modes, the electromagnetic intensity of the highest frequency bulk modes is integrated along the edge of the core. It is sufficient to perform such integration for either one of the two doubly degenerate modes, since the integrations for both modes are equal, as required by symmetry.

Figure 15B:
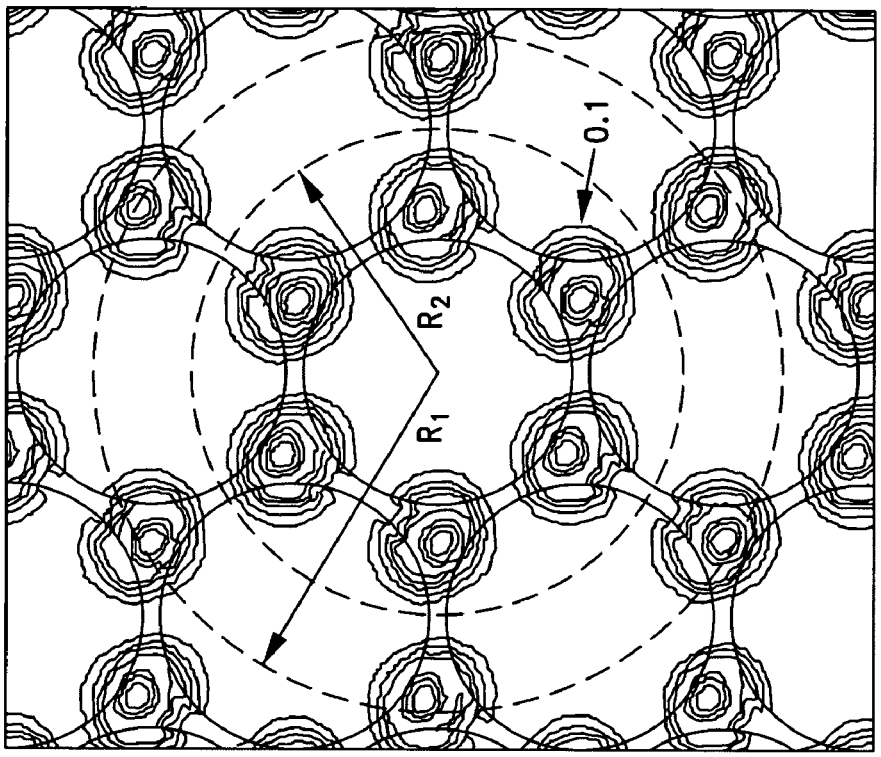
FIGS. 15A and 15B illustrate intensity contour maps of the two highest frequency doubly degenerate bulk modes below the bandgap at the Γ point, wherein $R_1$ is an example of a core radius that supports both core modes and surface modes, and $R_2$ is an example of a core radius that supports only core modes.
Figure 15A:
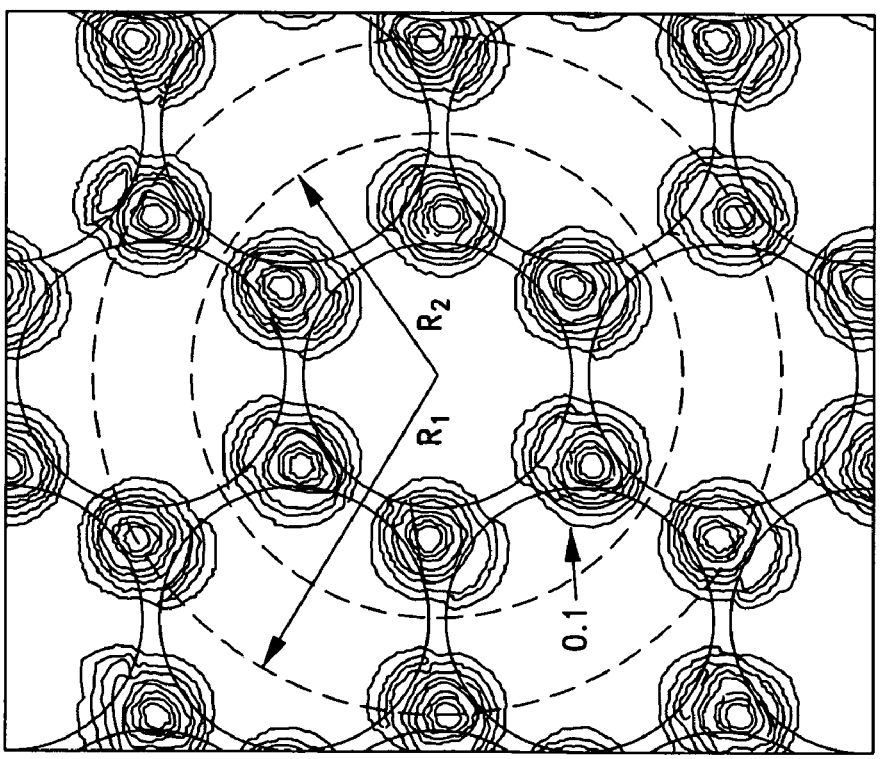

The foregoing determination of the radius R of the air core can be performed in accordance with a method of numerically computing the intensity distribution of the bulk modes of the infinite fiber cladding. In accordance with the method, the intensity distribution of the highest frequency bulk mode of the fiber of interest without the air core is first determined. Thereafter, a circular air core of radius R is superposed on that intensity distribution. As illustrated in FIGS. 15A and 15B, changing the core radius R causes the edge of the core to pass through different areas of this field distribution. In accordance with the computing method, the fiber will support surface modes when the edge of the core intersects high lobe regions of this field distribution. In FIGS. 15A and 15B, a core of radius $R=R_1$ is one example of a core radius that passes through several (six in this example) high intensity lobes of the highest frequency bulk mode. The computing method predicts that a core with such a radius will support surface modes. At the other extreme, when the core has a radius $R=R_2$, as illustrated in FIGS. 15A and 15B, the core edge does not pass through any of the high-intensity lobes of the bulk mode, and such a core of radius $R_2$ does not support surface modes.

Although, described in connection with a circular core, it should be understood that the foregoing method is not limited to circular cores, and the method is applicable to any core shape.

As described above, the computing method is qualitative. In accordance with the method, if the edge of a core of a selected radius R intersects high intensity lobes of the bulk mode, the fiber having a core of that radius will support surface modes. As described thus far, the method does not stipulate how many surface modes are supported. Furthermore, the method does not specify how high an intensity must be intersected by the edge of the core or how many high intensity lobes the edge of the core must intersect before surface modes appear (i.e., are supported).

The HFBM criterion is advantageously simplified by recognizing that the intensity lobes of the HFBM are nearly azimuthally symmetric, as shown in FIG. 5. Thus, the portion of each lobe confined in a dielectric corner 110 can be approximated by the circle 114 inscribed in the corner 110, as illustrated in FIG. 2. As discussed above, the radius α of the inscribed circle 114 is related to the period Λ and radius ρ of the holes 104 of the triangular pattern by $\alpha = (\Lambda/\sqrt{3}) - \rho$.

Figure 16:
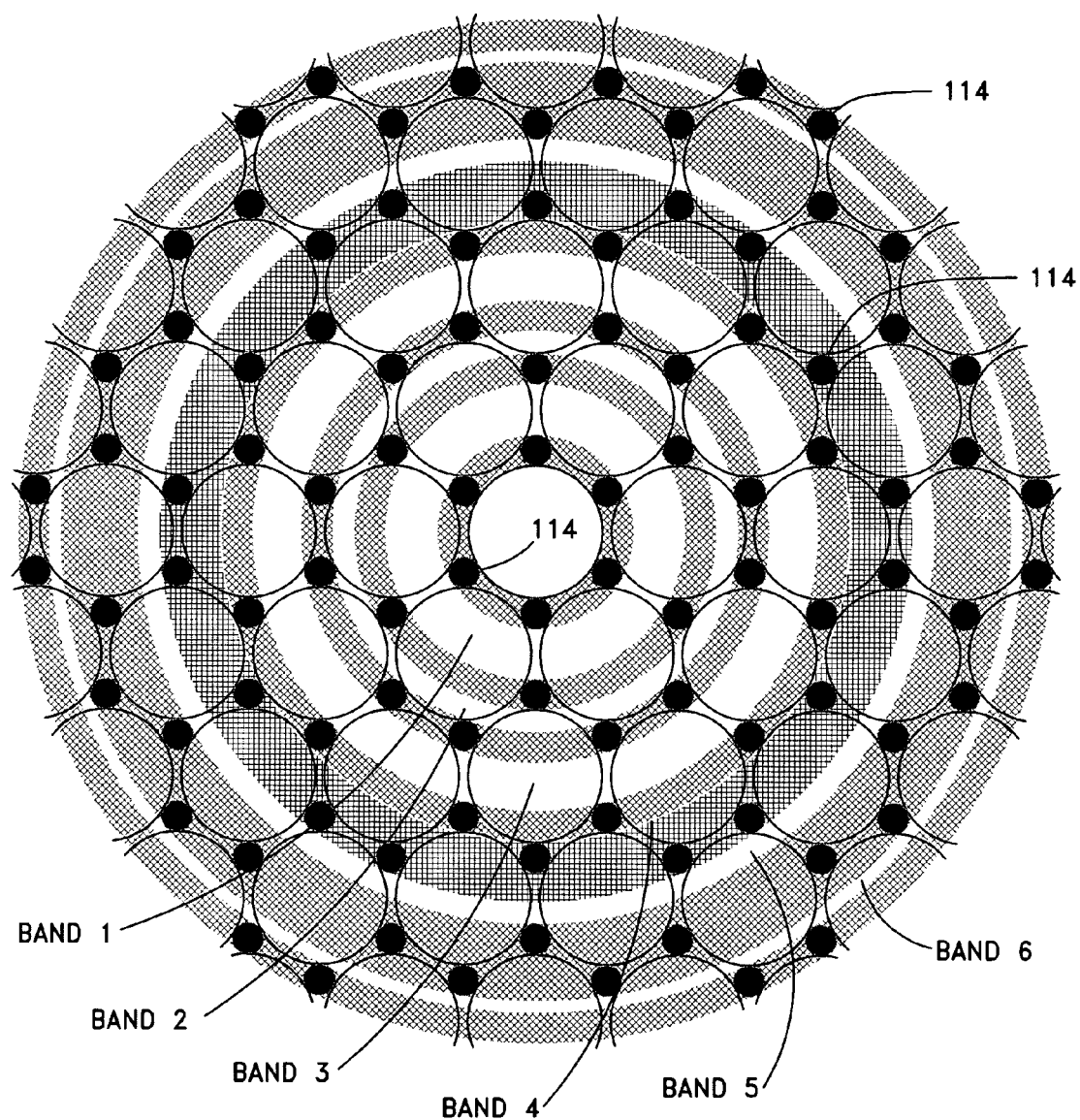
FIG. 16 illustrates a graphical representation of a partial cross section of the triangular pattern air core PBF, wherein black circles at each dielectric corner represent dielectric rods, and wherein unshaded rings represent bands of core radii for which the surface of the core does not intersect the dielectric rods.

The portions of the HFBM confined to the dielectric are approximated by a two-dimensional array of circles 114 centered on all the photonic-crystal corners 110, as illustrated in FIG. 16, which is plotted for a triangular pattern and ρ=0.47Λ. This approximation enables a new, simpler existence criterion to be formulated for surface modes: surface modes exist when and only when the surface of the core 106 intersects one or more of the circles 114. Of course, many other kinds of perturbations can induce surface modes in the photonic crystal 102, so that the foregoing condition for the absence of surface modes is a necessary condition but it is not always a sufficient condition.

The same geometric criterion can also be derived using coupled-mode theory. In view of the symmetry of the lower-band bulk modes, each corner 110 can be approximated by a dielectric rod inscribed in the corner 110, wherein the rod extends the length of the PBF 100. Each isolated rod is surrounded by air and constitutes a dielectric waveguide. The dielectric waveguide carries a fundamental mode with strong fields in the rod that decay evanescently into the surrounding air, so the field looks much like the individual lobes of the HFBM illustrated in FIG. 5. Thus, the periodic array of rods has the pattern of the circles 114 illustrated in FIG. 16. The waveguide modes of the individual rods are weakly coupled to each other due to the proximity of neighboring rods and form the bulk modes.

The HFBM is just one particular superposition of individual waveguide modes. If an air core 106 that cuts into one or more rods is introduced, the removal of dielectric perturbs the waveguide modes in the opposite direction to that forming bulk modes. The waveguide modes of the ring of perturbed rods intersected by the surface of the core 106 are then coupled to each other and form a surface mode. This surface mode is supported by the ring of rods and has fields that decrease outside each rod, as evidenced by the exemplary surface mode of FIG. 3. If the surface of the core 106 cuts only through membranes 112 instead of corners 110, the rods are unperturbed, and the modes couple to each other much as they did without the presence of the core 106. Thus, no surface mode is formed. In accordance with this description, surface modes exist if and only if the surface of the core 106 intersects rods. This is the same criterion that was derived above by approximating the HFBM lobes by the inscribed circles 114.

To verify the validity of this new geometric criterion, the criterion is applied to the most widely studied class of air-core PBFs, namely fibers with circular air holes in a triangular pattern, as illustrated in FIG. 16. The core 106 is a larger circular air hole of radius R at the center of the fiber 100. Again, this analysis postulates that when R is selected so that the surface of the core 106 intersects one or more rods (e.g., the circles 114 in FIG. 16), then surface modes will exist, and the number of surface modes will be proportional to the number of rods intersected. This scaling law is expected because as the number of intersected rods increases the perturbation magnitude increases and the number of surface modes also increases. Conversely, when the surface of the core 106 does not intersect any rods, no surface modes occur. A simple diagram of the fiber cross section, such as the diagram illustrated in FIG. 16, makes the application of this criterion to any fiber geometry very easy.

The result of the foregoing geometric analysis is graphed in FIG. 16 for a triangular pattern. The shaded (cross hatched) rings in FIG. 16 represent the ranges of core radii that intersect rods and thus support surface modes. As discussed above with respect to FIG. 11, the unshaded rings between the shaded rings (band 1-band 6) represent ranges of radii that intersect no rods and thus do not support surface modes. The dependence of the number of surface modes on the core radius is calculated straightforwardly by applying elementary trigonometry to FIG. 16 to determine the number of rods crossed by the surface of a core 106 of a given radius. The numbers are plotted as a solid curve in FIG. 17, wherein the horizontal axis of the graph is the core radius normalized to the crystal period Λ (e.g., R/Λ), and wherein the left vertical axis represents the number of rods intersected by the surface of the core, as predicted by the geometric criterion.

Figure 17:
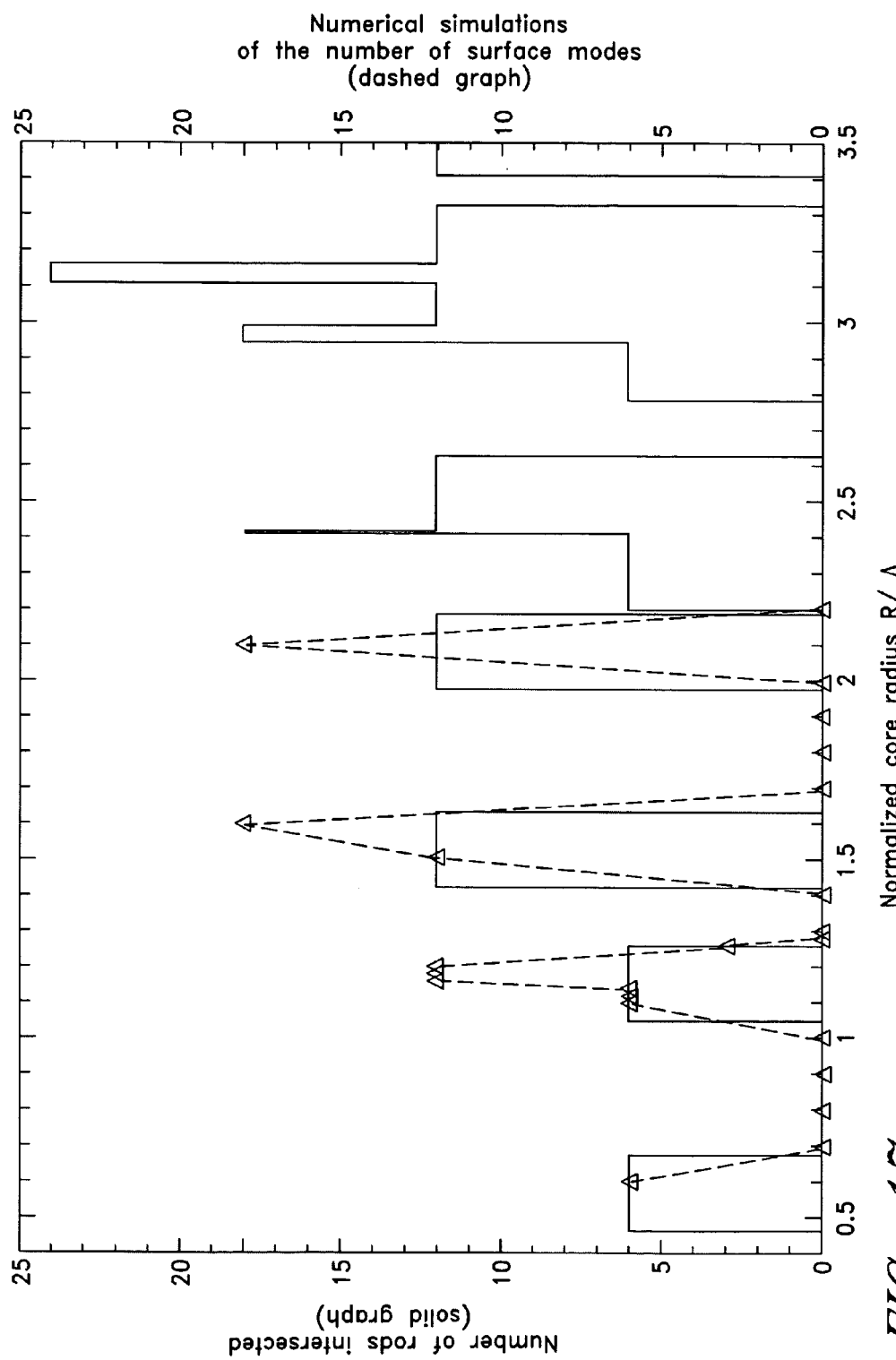
FIG. 17 illustrates a graph (dashed lines) of the results of the numerical simulations of the number of surface modes and illustrates a graph (solid lines) of the number of surface modes predicted using the geometric model of FIG. 16 and counting the number of rods intersected by the surface of the core, wherein the number of surface modes in each graph is plotted with respect to the normalized core radius R/Λ.

The simple postulate predicts the important result illustrated in FIG. 17 that several bands of radii for this type of PBF 100 support no surface modes at all across the entire bandgap. Six such bands occur in the range covered in FIG. 17 for radii R up to 3.5Λ, where Λ is the crystal period as defined above. The range in FIG. 17 does not encompass the band below R=0.47Λ, for which the radii are too small to support a core mode. Although not shown in FIG. 17, another eight bands occur for radii larger than 3.5Λ. The last band is at R approximately equal to 8.86 Λ.

Table 1 lists the boundaries and the widths of the 14 bands. As shown in Table 1, the first band is the widest. The first band is also the most important for most purposes because the first band is the only band that falls in the single-mode range of this PBF 100 (e.g., in the range where R is less than about 1.2 for an air-hole radius ρ equal to 0.47Λ). All other bands, except for the third one, are substantially narrower. Generally, the bands where no surface modes are supported become narrower as the radius of the core 106 increases. Note that by nature of the rod approximation, these values are independent of the refractive index of the crystal lattice dielectric 102.

TABLE 1

| Band No. | Range from geometric criterion (in units of Λ) | Range from HFBM criterion (in units of Λ) | Range from simulations (in units of Λ) | Width of Band (in units of Λ) |
|---|---|---|---|---|
| 1 | 0.685–1.047 | 0.68–1.05 | 0.65 ± 0.05–1.05 ± 0.05 | 0.363 |
| 2 | 1.262–1.420 | 1.26–1.43 | 1.27 ± 0.01–1.45 ± 0.05 | 0.158 |
| 3 | 1.635–1.974 | 1.64–1.97 | 1.65 ± 0.05–2.05 ± 0.05 | 0.339 |
| 4 | 2.189–2.202 | | | 0.013 |
| 5 | 2.624–2.779 | | | 0.155 |

TABLE 1-continued

| Band No. | Range from geometric criterion (in units of Λ) | Range from HFBM criterion (in units of Λ) | Range from simulations (in units of Λ) | Width of Band (in units of Λ) |
|---|---|---|---|---|
| 6 | 3.322–3.405 | | | 0.083 |
| 7 | 3.619–3.679 | | | 0.059 |
| 8 | 3.893–3.934 | | | 0.071 |
| 9 | 4.271–4.402 | | | 0.131 |
| 10 | 5.239–5.400 | | | 0.161 |
| 11 | 6.218–6.244 | | | 0.026 |
| 12 | 6.914–6.916 | | | 0.0022 |
| 13 | 7.875–7.914 | | | 0.039 |
| 14 | 8.844–8.856 | | | 0.0113 |

Location of the 14 bands of core radii that support no surface modes in triangular PBFs with $\rho = 0.47\Lambda$.

To evaluate the accuracy of the foregoing quantitative predictions, numerical simulations of the surface modes of this same class of PBFs were conducted on a supercomputer using a full-vectorial plane wave expansion method, as discussed above The dielectric was defined to be silica and the radius ρ of the air-holes 104 was defined to be equal to 0.47Λ. The results of the simulations are plotted in FIG. 17 as open triangles joined by dashes, wherein the right vertical axis represents the number of surface modes predicted by the numerical simulations. Note that this curve of triangular points is exactly the same as the curve of triangular points of FIG. 9. The agreement with the predictions of the geometric criterion (plotted as a solid curve in FIG. 17) is excellent. This agreement is further apparent by comparing the information in the second column of Table 1 for the boundary values of the first three surface-mode-free bands generated by the geometric criterion with the information in the fourth column of Table 1 for the boundary values produced by the simulations. The geometric criterion produces values that are within 5% of the values produced by the simulations. Note that the exact boundary radii produced by the simulations were computed in limited numbers (e.g., for the radii encompassing the first three surface-mode-free bands) and were computed with a limited number of digits because the simulations are very time consuming (e.g., about six hours per radius). In contrast, the geometric criterion provided far more information in a small amount of time. Also note that although the geometric criterion does not accurately predict the exact number of surface modes (see FIG. 17), the geometric criterion does exhibit the correct trend. In particular, the geometric criterion predicts that surface modes generally become more numerous with increasing radius R of the core 106, which is consistent with the original hypothesis.

Figure 18:
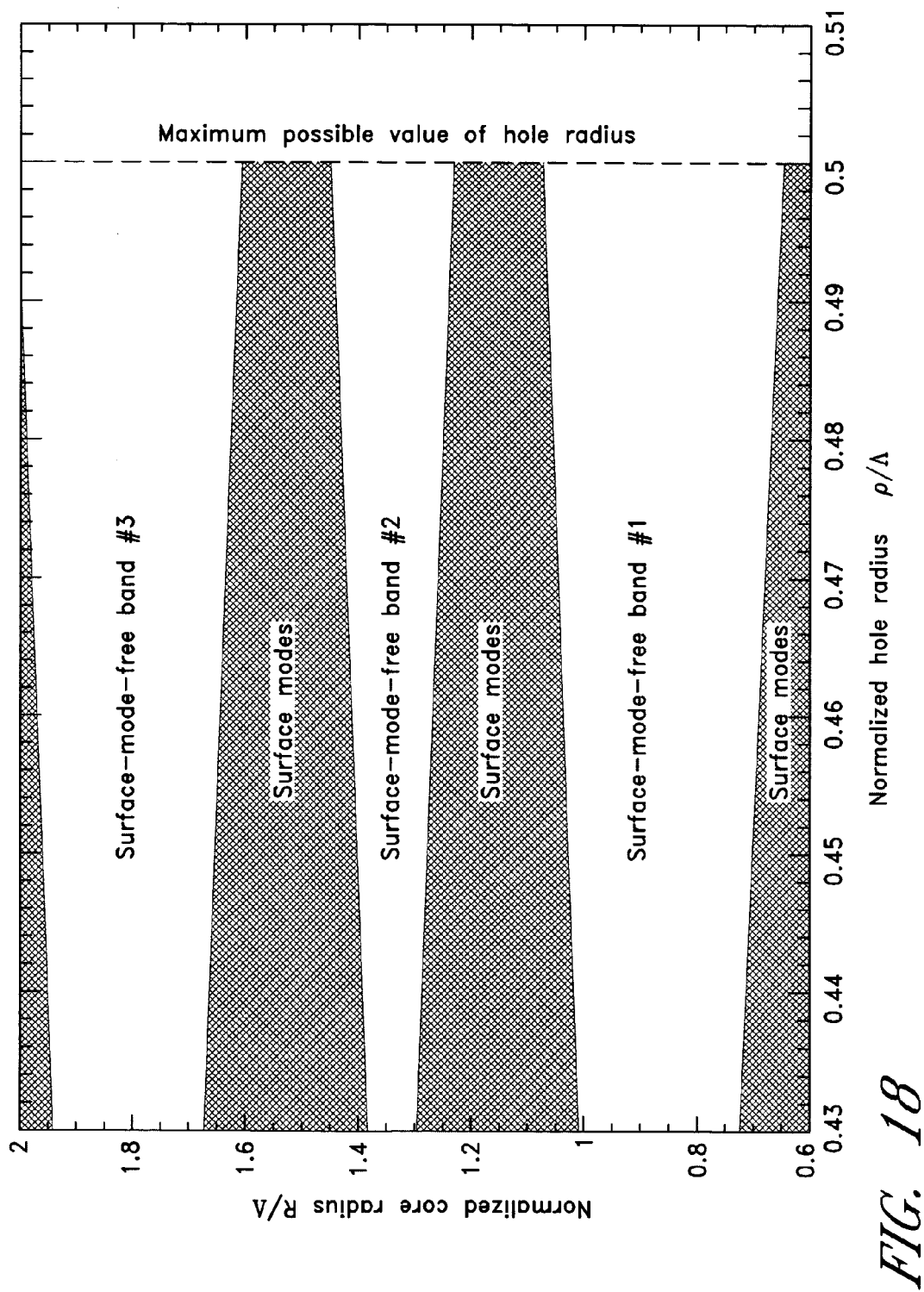
FIG. 18 illustrates a plot of the normalized core radius R/Λ versus the normalized hole radius ρ/Λ to show the effect of the fiber air-filling ratio on the presence of surface modes.

The effect of the fiber air-filling ratio on the presence of surface modes can also be quickly evaluated with the above-described geometric criterion by simply recalculating the boundary radii for different values of the hole radius ρ. The results of the calculations are illustrated in FIG. 18, which plots the normalized boundary core radius R/Λ, from R/Λ=0.6 to R/Λ=2.0, on the vertical axis versus the normalized hole radius ρ/Λ, from ρ/Λ=0.43 to ρ/Λ=0.50, on the horizontal axis. The possible values for ρ are constrained between approximately 0.43Λ, below which the photonic crystal has no bandgap, and below approximately 0.50Λ, at which the thickness of the membranes 112 becomes zero. The ranges of core radii versus hole radii that support surface modes are shaded (cross hatched) and the ranges of core radii that do not support surface modes are unshaded. FIG. 18 shows that larger holes 104, which have greater air-filling ratios, yield wider surface-mode-free bands because increasing the radius ρ of the air-holes 110 decreases the radius α of the rods (represented by the inscribed circles 114). Because of the smaller rod size, the ranges of core radii R that intersect the rods are narrower, and the bands of surface-mode-free radii become wider.

Other interesting observations can be obtained from the results of the studies described above. First, in experimental PBFs 100, the core 106 is typically created by removing the central seven tubes or the central nineteen tubes from the preform. These configurations correspond to core radii R of approximately 1.15Λ and approximately 2.1Λ, respectively. The geometric criterion defined herein confirms the predictions of exact simulations that both of these configurations exhibit surface modes, as shown, for example, in FIG. 17. The existence of the surface modes explains, at least in part, the high propagation loss of most photonic-bandgap fibers fabricated to date.

Second, the simulated curve in FIG. 17 shows that a small change in core radius is all it takes to go from a surface-mode-free PBF to a PBF that supports surface modes. The abruptness of the transitions is consistent with the perturbation process that creates surface modes, and supports the credibility of the rod approximation discussed above.

Third, the trends in Table 1 discussed earlier can be explained with simple physical arguments. As the core radius increases, adjacent concentric layers of rods become closer to each other, as shown in FIG. 16. For larger radii, it is increasingly more difficult to find room for a circular radius that avoids all rods. Also, a larger radius tends to intersect more rods, and thus the number of surface modes generally increases. A manifestation of this effect can readily be seen in the fifth and sixth layers of rods, which lie between band 4 and band 5 in FIG. 16. The fifth and sixth layers overlap radially and thus merge into a single, wider zone of core radii that support surface modes. In other words, there is no surface-mode-free band between the fifth and sixth layers of rods. The same effect occurs with respect to the seventh, eighth and ninth layers, which lie between band 5 and band 6 in FIG. 16 and cause the large numerical difference between the maximum radius of band 5 (R=2.779Λ) and the minimum radius of band 6 (R=3.322Λ) in Table 1. Conversely, as the radius R of the core 106 increases, the surface-mode-free bands become increasingly narrower, as can readily be seen in the fifth column of Table 1, which lists the width of each surface-mode-free band in units of Λ.

It can be expected intuitively that cores 106 with radii larger than some critical value $R_c$ will all support surface modes, and thus, only a finite number of surface-mode-free bands are available. This intuitive expectation is consistent with the results of Table 1. In particular, for the structure evaluated herein for a radius ρ of the holes 104 of 0.47Λ, the number of surface-mode-free bands is limited (i.e., only 14 bands), and a critical radius $R_c$ (i.e., approximately 8.86Λ) exists above which the surface modes form a continuum. As indicated by the values in Table 1, the last four surface-mode-free bands are so narrow (e.g., ΔR of a few percent of Λ) that the last four bands are probably unusable for most practical applications. A corollary of this observation is that multimode PBFs with the particular geometry illustrated herein and with a core radius R greater than 5.4Λ will likely be plagued with surface modes.

The average value of the $1/e^2$ radius of any of the lobes of the actual bulk mode in FIGS. 15A and 15B is approximately 0.22Λ. In comparison to the intensity lobe, the radius α of the inscribed (dashed) circle in FIG. 8 is approximately 0.107Λ. A more refined figure and a better quantitative agreement can be obtained by refining the value of the equivalent radius α of the silica rod, and by calculating the average radius of the fundamental mode of a solid rod suspended in air.

Figure 19:
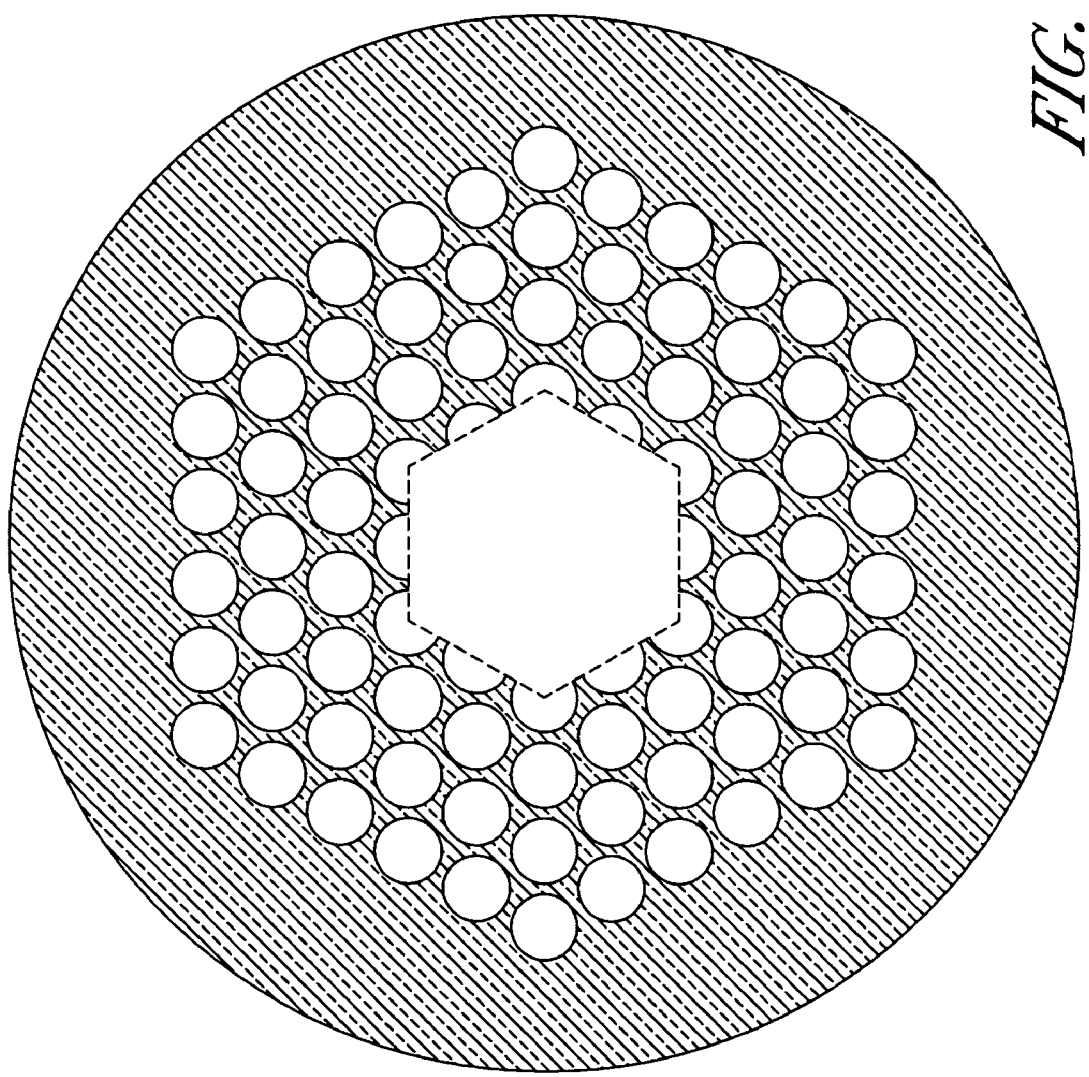
FIG. 19 schematically illustrates a cross section of an alternative air-core photonic bandgap fiber having a non-circular (e.g., hexagonal) core shape and no surface modes.

A final observation obtained from the study described herein is that surface modes can be avoided in principle for any core size by selecting a non-circular core shape having a surface that does not intersect any rods. A schematic of an example of a non-circular core having a characteristic dimension corresponding to the shortest distance from the center to the nearest boundary of the core is shown in FIG. 19. With a hexagon-shaped core (as outlined by a dashed line in FIG. 19 to assist in visualizing the shape of the core), the introduction of any surface mode is avoided even when the core region is large. Such a structure could represent an improvement over the above-described circular core structures in applications where multi-mode operation is desired.

The geometric criterion described herein is not limited to the particular triangular geometry with circular cladding holes and the circular cores. It is applicable to other shapes and geometries.

In accordance with the foregoing description, a simple geometric criterion quickly evaluates whether an air-core PBF exhibits surface modes. Comparison of the results of the geometric criterion to the results of numerical simulations demonstrates that when applied to fibers with a triangular-pattern cladding and a circular core, the geometric criterion accurately predicts the presence of a finite number of bands of core radii that support no surface modes. For sufficiently large circular cores (i.e., for radii above the largest of these bands), the fiber supports surface modes for any core radius. This versatile criterion provides an expedient new tool to analyze the existence of surface modes in photonic-crystal fibers with an arbitrary crystal structure and an arbitrary core profile.

Figure 20A:
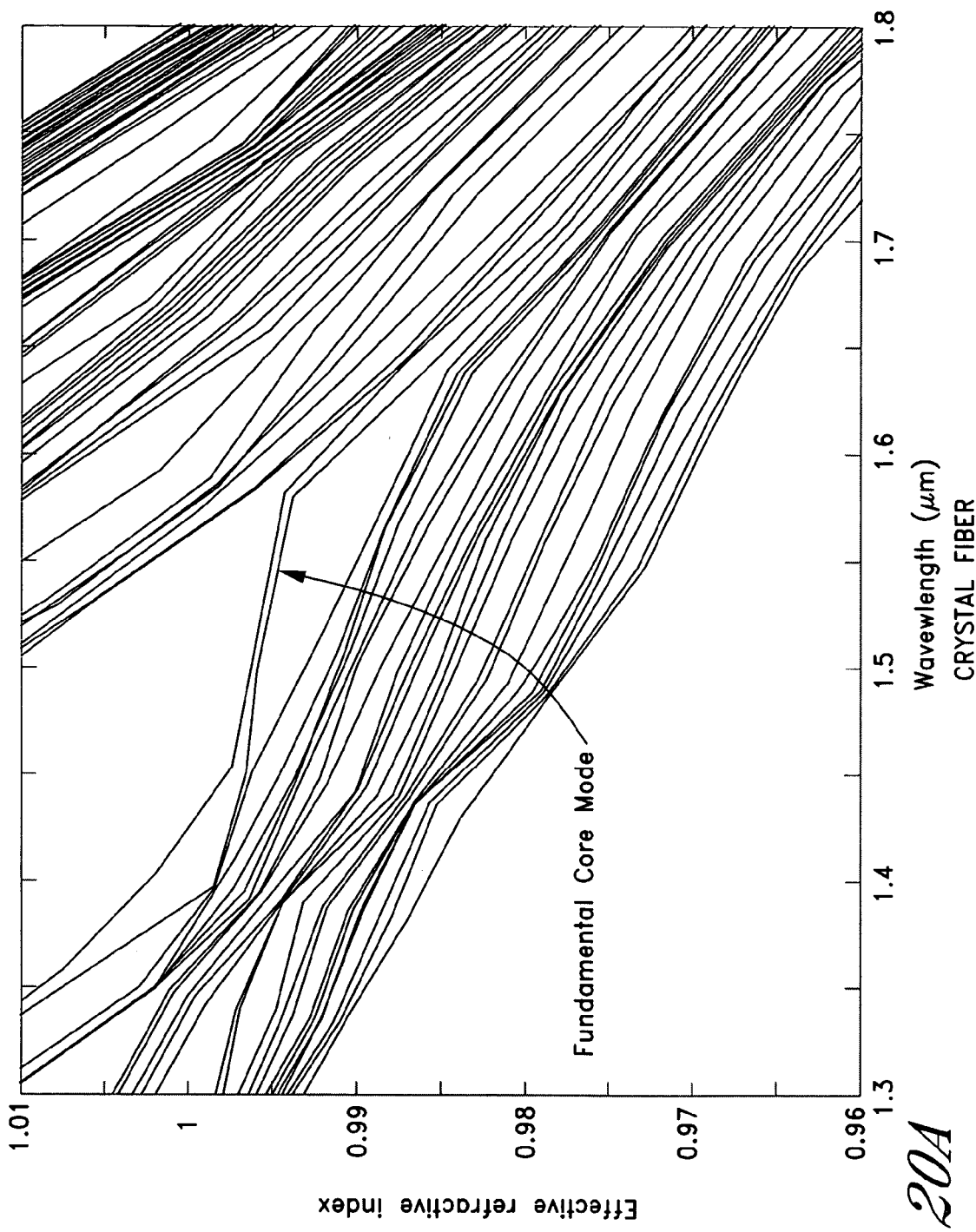
FIGS. 20A and 20B illustrate for comparison the effective refractive indices of core modes and surface modes for two commercially available photonic bandgap fibers.
Figure 20B:
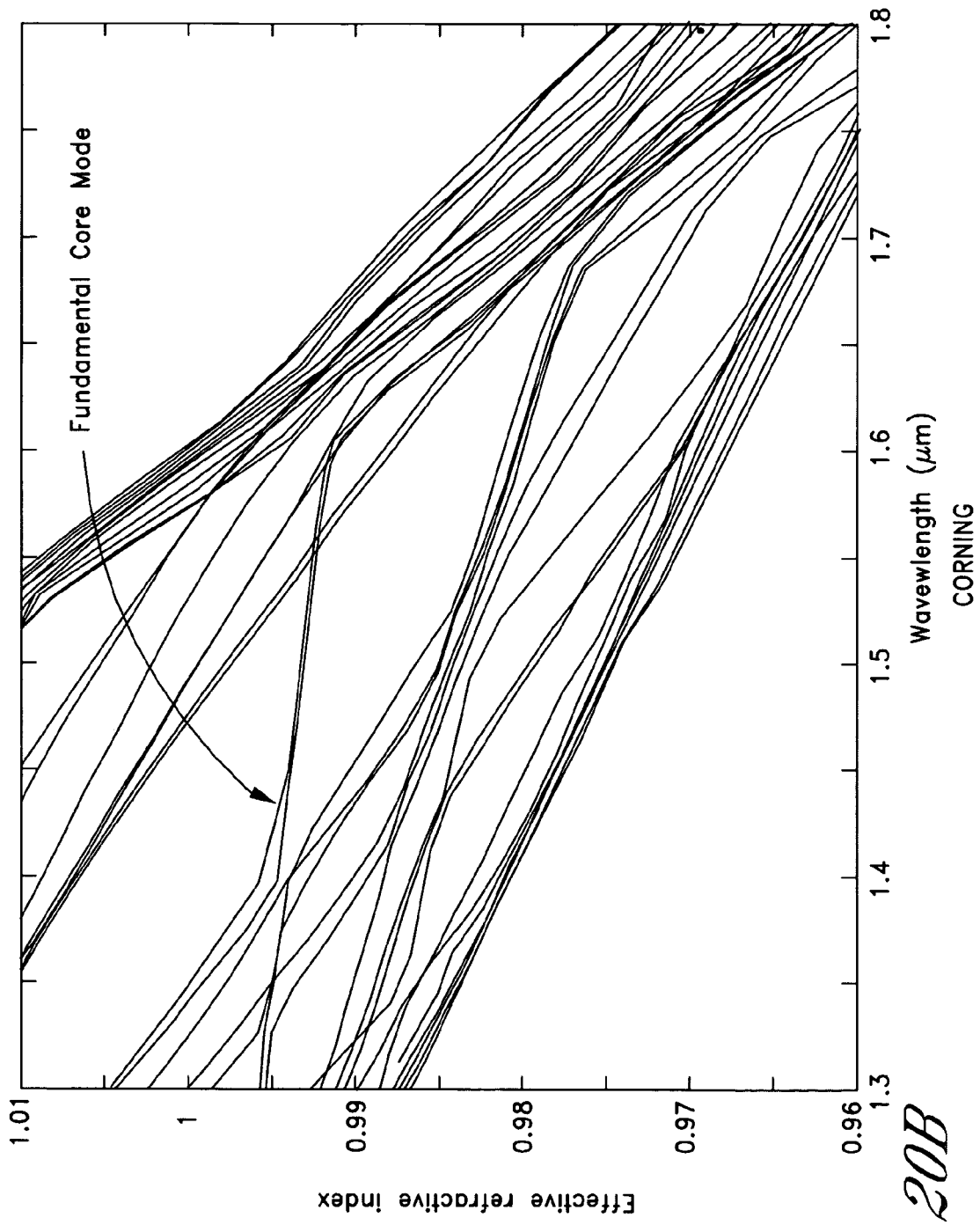

FIGS. 20A and 20B illustrate plots of the effective refractive indices of the modes as a function of wavelength. The plot in FIG. 20A illustrates indices of the fiber manufactured by Crystal Fibre. The plot in FIG. 20B illustrates the indices of the fiber manufactured by Corning. The plots were generated using numerical simulations. The fundamental core modes are shown in bold curves, and the less intense lines are the surface modes. The Crystal Fibre core mode (FIG. 20A) has a measured minimum loss of the order of 100 dB/km while the Corning core mode (FIG. 20B) has a measured minimum loss of 13 dB/km. The loss of the core mode is believed to be mainly due to coupling of the core mode to surface modes, which are inherently lossy due to the concentration of energy near the surface of the core. Hence surface modes suffer from enhanced Rayleigh scattering. The total power coupled from core modes to surface modes will be enhanced, and thus the loss will be larger, if the core supports a large number of surface modes. In addition, it is well known from coupled mode theory that the coupling of two modes, in this case the core mode to a surface mode, will be stronger when the effective refractive indexes of the two modes are closer.

When considering the modes at a wavelength of 1.50 μm in FIGS. 20A and 20B, it can be seen that there are far more surface modes in the Crystal Fibre structure (FIG. 20A) than in the Corning structure (FIG. 20B). Furthermore, the effective refractive indices of the Corning surface modes are less than 0.986, while the core mode has an effective refractive index of 0.994, a 0.8% difference. On the other hand, the core mode in the Crystal Fibre structure has an effective refractive index of 0.996, while the nearest surface mode has an effective refractive index of 0.994, only a 0.2% difference. Everything else being the same, in particular the level of geometrical perturbation present in the core of the two fibers, coupling of the core mode to surface modes is expected to be stronger in the fiber manufactured by Crystal Fibre. Thus, the Crystal Fibre fiber supports more surface modes, and the surface modes couple more strongly, which is consistent with the higher propagation loss of the Crystal Fibre fiber. From the foregoing, it can be concluded that to design air-guided PBFs with a low loss, the preferred approach is to completely eliminate surface modes, as described above. If it is not possible to completely eliminate the surface modes, a second approach is to reduce the number of surface modes (e.g., by assuring that the core does not cut through too many corners of the cladding lattice), to increase the effective index detuning between the core modes and the remaining surface modes, or both.

Although described above in connection with particular embodiments of the present invention, it should be understood that the descriptions of the embodiments are illustrative of the invention and are not intended to be limiting. Various modifications and applications may occur to those skilled in the art without departing from the true spirit and scope of the invention as defined in the appended claims.

What is claimed is:

1. A method of making a photonic-bandgap fiber comprising a material with a pattern of regions therein that form a crystal lattice, the material having a first refractive index and the pattern of regions having a second refractive index lower than the first refractive index, the method comprising:
    determining intensity profiles of a highest frequency bulk mode proximate to the regions; and
    forming a central core in the crystal lattice, the core having an edge that intersects the pattern of regions at locations where the intensities of the highest frequency bulk mode are low enough that the fiber supports no surface modes.

2. The method of claim 1, wherein the pattern is periodic.

3. The method as defined in claim 1, wherein:
    the regions in the material are circular;
    the pattern of regions is arranged such that each group of three adjacent regions forms a triangle with a respective first portion of the material between each pair of regions and with a respective second portion of the material forming a central area within each group of three adjacent regions; and
    the central core is formed in the crystal lattice such that the edge of the central core passes only through the first portions of the material.

4. The method as defined in claim 3, wherein the regions in the material are holes having walls defined by the surrounding material.

5. The method as defined in claim 4, wherein the holes in the material are hollow.

6. The method as defined in claim 5, wherein the holes in the material are filled with air having the second refractive index.

7. The method as defined in claim 5, wherein the holes in the material are filled with a gas having the second refractive index.

8. The method as defined in claim 5, wherein the holes in the material are filled with a liquid having the second refractive index.

9. The method as defined in claim 3, wherein the circular regions comprise a solid having the second refractive index.

10. The method as defined in claim 1, wherein the material is a dielectric.

11. The method as defined in claim 1, wherein the material is silica.

12. A photonic-bandgap fiber comprising:

a crystal lattice comprising a first material having a first refractive index, the first material having a pattern of a second material formed therein, the second material having a second refractive index lower than the first refractive index, the crystal lattice having a plurality of first regions that support intensity lobes of the highest frequency bulk mode and having a plurality of second regions that do not support intensity lobes of the highest frequency bulk mode; and a central core formed in the crystal lattice, the central core having an edge that passes only through the second regions of the dielectric;

wherein the pattern of the second material comprises a plurality of geometric regions, each geometric region having a respective center and adjacent geometric regions being spaced apart by a center-to-center distance $\Lambda$;

wherein each geometric region of the second material is circular and has a radius $\rho$, the radius $\rho$ being less than $0.5\Lambda$;

wherein the pattern is triangular; and wherein the first regions comprise circles inscribed between three adjacent geometric regions, each circle having a radius a equal to $(\Lambda/\sqrt{3})-\rho$.

13. A photonic-bandgap fiber comprising:

a crystal lattice comprising a first material having a first refractive index, the first material having a pattern of a second material formed therein, the second material having a second refractive index lower than the first refractive index, the crystal lattice having a plurality of first regions that support intensity lobes of the highest frequency bulk mode and having a plurality of second regions that do not support intensity lobes of the highest freciuency bulk mode; and a central core formed in the crystal lattice, the central core having an edge that passes only through the second regions of the dielectric;

wherein the pattern of the second material comprises a plurality of geometric regions, each geometric region having a respective center and adjacent geometric regions being spaced apart by a center-to-center distance $\Lambda$;

wherein each geometric region of the second material is circular and has a radius$\rho$, the radius $\rho$ being less than $0.5\Lambda$;

wherein the pattern is triangular; and wherein;

the radius $\rho$ of each geometric region is approximately $0.47\Lambda$;

the edge of the core has a radius within a range of core radii that extends from a radius of approximately $0.68\Lambda$ to a radius of approximately $1.05\Lambda$; and the fiber is single mode.

14. A photonic-bandgap fiber comprising:

a crystal lattice comprising a first material having a first refractive index, the first material having a pattern of a second material formed therein, the second material having a second refractive index lower than the first refractive index, the crystal lattice having a plurality of first regions that support intensity lobes of the highest frequency bulk mode and having a plurality of second regions that do not support intensity lobes of the highest frequency bulk mode; and a central core formed in the crystal lattice, the central core having an edge that passes only through the second regions of the dielectric;

wherein the pattern of the second material comprises a plurality of geometric regions, each geometric region having a respective center and adjacent geometric regions being spaced apart by a center-to-center distance $\Lambda$;

wherein each geometric region of the second material is circular and has a radius $\rho$, the radius $\rho$ being less than $0.5\Lambda$;

wherein the pattern is triangular; and wherein:

the radius $\rho$ of each geometric region is approximately $0.47\Lambda$;

the edge of the core has a radius within one of a plurality of ranges of radii;

a first of the plurality of ranges of core radii extends from a radius of approximately $0.68\Lambda$ to a radius of approximately $1.05\Lambda$;

a second of the plurality of ranges of core radii extends from a radius of approximately $1.26\Lambda$ to a radius of approximately $1.43\Lambda$; and a third of the plurality of ranges of core radii extends from a radius of approximately $1.64\Lambda$ to a radius of approximately $1.97\Lambda$.

15. A photonic-bandgap fiber comprising:

a crystal lattice comprising a first material having a first refractive index, the first material having a pattern of a second material formed therein, the second material having a second refractive index lower than the first refractive index, the crystal lattice having a plurality of first regions that support intensity lobes of the highest frequency bulk mode and having a plurality of second regions that do not support intensity lobes of the highest frequency bulk mode; and a central core formed in the crystal lattice, the central core having an edge that passes only through the second regions of the dielectric;

wherein the pattern of the second material comprises a plurality of geometric regions, each geometric region having a respective center and adjacent geometric regions being spaced apart by a center-to-center distance $\Lambda$;

wherein each geometric region of the second material is circular and has a radius $\rho$, the radius $\rho$ being less than $0.5\Lambda$;

wherein the pattern is triangular; and wherein:

the radius $\rho$ of each geometric region is approximately $0.47\Lambda$;

the edge of the core has a radius within one of a plurality of ranges of radii;

the first of the plurality of ranges of core radii extends from a radius of approximately $0.685\Lambda$ to a radius of approximately $1.047\Lambda$;

the second of the plurality of ranges of core radii extends from a radius of approximately $1.262\Lambda$ to a radius of approximately $1.420\Lambda$; and the third of the plurality of ranges of core radii extends from a radius of approximately $1.635\Lambda$ to a radius of approximately $1.974\Lambda$.

16. A geometric method for selecting the dimensions of a core for producing a photonic-bandgap fiber free of surface modes, the photonic-bandgap fiber having a crystal lattice comprising a first material having a first refractive index, the material encompassing a periodic pattern of regions of a second material, the second material having a second refractive index lower than the first refractive index, each region of the second material spaced apart from an adjacent region of the second material by a membrane of the first material and each intersection of membranes forming a vein of the first material, the method comprising:
- defining an inscribed central area within each vein of the second material such that an outer periphery of the inscribed central area is tangential to the outer peripheries of the adjacent regions around the vein;
- defining a plurality of ranges of core characteristic dimensions wherein any core having a dimension within one of the plurality of ranges has an edge that does not pass through any of the inscribed central areas; and
- selecting a core having a dimension within one of the plurality of ranges of core characteristic dimensions.

17. The geometric method of claim 16, wherein:
- each region has a respective center and adjacent regions are spaced apart by a center-to-center distance $\Lambda$;
- each region of the second material is circular and has a radius $\rho$, the radius $\rho$ being less than $0.5\Lambda$; and
- the pattern is triangular.

18. The geometric method of claim 17, wherein the inscribed central area is a circle having a radius a equal to $(\Lambda/\sqrt{3})-\rho$.

19. The geometric method of claim 17, wherein:
- the radius $\rho$ of each geometric region is approximately $0.47\Lambda$;
- the edge of the core has a radius within a range of core radii that extends from a radius of approximately $0.68\Lambda$ to a radius of approximately $1.05\Lambda$; and
- the fiber is single mode.

20. The geometric method of claim 17, wherein:
- the radius $\rho$ of each region is approximately $0.47\Lambda$;
- the core is generally circular and the core characteristic dimension, is the radius of the core;
- a first of the plurality of ranges of core characteristic dimensions extends from a radius of approximately $0.68\Lambda$ to a radius of approximately $1.05\Lambda$;
- a second of the plurality of ranges of core characteristic dimensions extends from a radius of approximately $1.26\Lambda$ to a radius of approximately $1.43\Lambda$; and
- a third of the plurality of ranges of core characteristic dimensions extends from a radius of approximately $1.64\Lambda$ to a radius of approximately $1.97\Lambda$.

21. The geometric method of claim 17, wherein:
- the radius $\rho$ of each region is approximately $0.47\Lambda$;
- the core is generally circular and the core characteristic dimension is the radius of the core;
- the first of the plurality of ranges of core characteristic dimensions extends from a radius of approximately $0.685\Lambda$ to a radius of approximately $1.047\Lambda$;
- the second of the plurality of ranges of core characteristic dimensions extends from a radius of approximately $1.262\Lambda$ to a radius of approximately $1.420\Lambda$; and
- the third of the plurality of ranges of core characteristic dimensions extends from a radius of approximately $1.635\Lambda$ to a radius of approximately $1.974\Lambda$.

* * * * *

UNITED STATES PATENT AND TRADEMARK OFFICE
CERTIFICATE OF CORRECTION

PATENT NO.      : 7,110,650 B2
APPLICATION NO. : 10/938755
DATED           : September 19, 2006
INVENTOR(S)     : Hyang Kyun Kim et al.

It is certified that error appears in the above-identified patent and that said Letters Patent is hereby corrected as shown below:

In column 5, line 9, please delete "α" and insert -- a --, therefor.

In column 5, line 9, please delete "a" and insert -- α --, therefore

In column 7, line 16, please delete "1. 15Λ," and insert -- 1.15Λ, --, therefor.

In column 7, line 33, please delete "rings;" and insert -- rings); --, therefor.

In column 8 (equation), line 59 (approx.), please delete "a=" and insert -- α= --, therefor.

In column 9, line 2, after "core" insert -- . --.

In column 9, line 67, please delete "8 Λx8Λ." and insert -- 8Λx8Λ. --, therefor.

In column 10, line 17, please delete "p=" and insert -- ρ= --, therefor.

In column, 10, line 36, please delete "π" and insert -- ρ --, therefor.

In column 14, line 37 (approx.), please delete "thee" and insert -- the --, therefor.

In column 16 (Table 1), line 62 (approx.), please delete "0.01" and insert -- 0.01 --, therefor.

In column 21, line 27 (approx.), in Claim 12, delete "a" and insert -- α --, therefor.

In column 21, line 37 (approx.), in Claim 13, delete "freciuency" and insert -- frequency --, therefor.

In column 21, line 47, in Claim 13, delete "radiusρ," and insert -- radius ρ, --, therefor.

In column 21, line 51 (approx.), in Claim 13, delete "wherein;" and insert -- wherein: --, therefor.

UNITED STATES PATENT AND TRADEMARK OFFICE
CERTIFICATE OF CORRECTION

PATENT NO. : 7,110,650 B2
APPLICATION NO. : 10/938755
DATED : September 19, 2006
INVENTOR(S) : Hyang Kyun Kim et al.

It is certified that error appears in the above-identified patent and that said Letters Patent is hereby corrected as shown below:

In column 23, line 20, in Claim 18, delete "a" and insert -- $\alpha$ --, therefor.

In column 24, line 4, in Claim 20, delete "dimension," and insert -- dimension --, therefor.

Signed and Sealed this

Sixth Day of February, 2007

JON W. DUDAS
*Director of the United States Patent and Trademark Office*